United States Patent
Ohya et al.

(10) Patent No.: US 11,185,561 B2
(45) Date of Patent: Nov. 30, 2021

(54) METHOD AND COMPOSITION FOR PREVENTING EGG ALLERGY

(71) Applicant: National Center for Child Health and Development, Tokyo (JP)

(72) Inventors: Yukihiro Ohya, Tokyo (JP); Shigenori Kabashima, Tokyo (JP); Osamu Natsume, Tokyo (JP); Hirohisa Saito, Tokyo (JP)

(73) Assignee: NATIONAL CENTER FOR CHILD HEALTH AND DEVELOPMENT, Tokyo (JP)

( * ) Notice: Subject to any disclaimer, the term of this patent is extended or adjusted under 35 U.S.C. 154(b) by 0 days.

(21) Appl. No.: 15/881,302

(22) Filed: Jan. 26, 2018

(65) Prior Publication Data

US 2018/0214494 A1 Aug. 2, 2018

Related U.S. Application Data

(60) Provisional application No. 62/451,671, filed on Jan. 28, 2017.

(51) Int. Cl.
| | | |
|---|---|---|
| *A61K 35/57* | (2015.01) | |
| *A61P 43/00* | (2006.01) | |
| *A61K 9/00* | (2006.01) | |
| *A61K 38/17* | (2006.01) | |

(52) U.S. Cl.
CPC ............ *A61K 35/57* (2013.01); *A61K 9/0095* (2013.01); *A61K 38/17* (2013.01); *A61P 43/00* (2018.01)

(58) Field of Classification Search
CPC .......... A61K 38/17; A61K 35/57; A61P 43/00
See application file for complete search history.

(56) References Cited

U.S. PATENT DOCUMENTS

| | | | | |
|---|---|---|---|---|
| 2007/0231448 A1* | 10/2007 | Takahashi | ............. | A21D 2/262 426/614 |
| 2011/0183062 A1* | 7/2011 | Ursel | ..................... | A23L 33/40 426/632 |
| 2016/0051639 A1* | 2/2016 | Raff | .................. | A61K 38/1735 424/94.61 |

OTHER PUBLICATIONS

John Wei-Liang Tan, MD, et al. A randomized trial of egg introduction from 4 months of age in infants at risk for egg allergy p. 1621-1628, received for publication Mar. 1, 2016, available online Oct. 11, 2016.

(Continued)

*Primary Examiner* — Johann R Richter
*Assistant Examiner* — Danielle Sullivan
(74) *Attorney, Agent, or Firm* — Kristina Castellano; Castellano PLLC

(57) ABSTRACT

The present invention provides an egg allergy prevention method to be carried out with respect to a human infant, including: a first administration period (first administration step) in which to administer, to an infant, heated egg white protein in an amount of 10 mg to 20 mg per day; and a second administration period (second administration step) which is a period after the first administration period and in which to administer, to the infant, the heated egg white protein in an amount of 65 mg to 90 mg per day.

8 Claims, 15 Drawing Sheets

(56) References Cited

OTHER PUBLICATIONS

Johanna Bellach, et al. Randomized placebo-controlled trial of hen's egg consumption for primary prevention in infants p. 1591-1599, received for publication Feb. 19, 2016, available online Aug. 12, 2016.

Debra J. Palmer, PhD, et al. Randomized controlled trial of early regular egg intake to prevent egg allergy p. 1600-1607, received for publication Jan. 30, 2016, available online Aug. 20, 2016.

Perkin MR, Logan K, Tseng A, et al. Randomized trial of introduction of allergenic foods in breast-fed infants. N Engl J Med 2016; 374: 1733-43, May 5, 2016.

Palmer DJ, Metcalfe J, Makrides M, et al. Early regular egg exposure in infants with eczema: a randomized controlled trial. J Allergy Clin Immunol 2013; 132: 387-92.e1, received for publication Jan. 13, 2013, available online Jun. 26, 2013.

Du Toit G, Roberts G, Sayre PH, et al. Randomized trial of peanut consumption in infants at risk for peanut allergy. N Engl J Med 2015; 372: 803-13, Feb. 26, 2015.

Kull I, Bergstrom A, Lilja G, Pershagen G, Wickman M. Fish consumption during the first year of life and development of allergic diseases during childhood. Allergy 2006; 61: 1009-15, accepted for publication Feb. 16, 2006.

Roduit C, Frei R, Depner M, et al. Increased food diversity in the first year of life is inversely associated with allergic diseases. J Allergy Clin Immunol 2014; 133: 1056?64, received for publication Apr. 16, 2013, available online Feb. 6, 2014.

Katz Y, Rajuan N, Goldberg MR, et al. Early exposure to cow's milk protein is protective against IgE-mediated cow's milk protein allergy. J Allergy Clin Immunol 2010; 126: 77-82.e1, Received for publication Jan. 25, 2010, available online Jun. 11, 2010.

Koplin JJ, Osborne NJ, Wake M, et al. Can early introduction of egg prevent egg allergy in infants? A population-based study. J Allergy Clin Immunol 2010; 126: 807-13, received for publication May 10, 2010, dated Oct. 2010.

Specification4_PETIT study 20161208 ver6 dated Sec. 8, 2016, National Center for Child Health and Development, and English language translation thereof.

Specification3_Lancet(comment) "Another step towards prevention of food allergy", published online Dec. 8, 2016.

Specification2_Lancet(appendix), "Two-step Egg Introduction for preventing egg allergy in High-risk Infants with eczema (PETIT study): a double-blind, placebo-controlled, parallel-group randomised clinical trial", Supplement to study published on Dec. 8, 2016.

Specification1_Lancet(the text), "Two-step Egg Introduction for preventing egg allergy in High-risk Infants with eczema (PETIT): a randomised, double-blind, placebo-controlled trial", published on Dec. 8, 2016.

\* cited by examiner

FIG. 11

Table E1. Participants who withdrew from the trial.

| Allocation | Age at withdrawal (months) | Reason for withdrawal | Allergic reaction caused by the trial powder |
|---|---|---|---|
| Egg group | 11 | Moved | None |
| Egg group | 11 | Refused to undergo oral food challenge for assessment of primary outcome | None |
| Egg group | 10 | Stopped taking the powder and started to eat whole hen's egg | None |
| Placebo group | 10 | Onset of cow's milk allergy caused voluntarily withdrawing | No |

FIG. 12

Table E2. Details of Baseline Characteristics

| Characteristic | Placebo group (N=61) | | Egg group (N=60) | | P value |
|---|---|---|---|---|---|
| | Missing value | n (%) | Missing value | n (%) | |
| Male sex | 0 | 40 (65.6%) | 0 | 39 (65.0%) | 1.00 |
| Caesarean section | 8 | 6 (11.3%) | 3 | 8 (14.0%) | 0.78 |
| Paternal history of allergic disease | 1 | 34 (56.7%) | 3 | 40 (70.2%) | 0.13 |
| Maternal history of allergic disease | 1 | 37 (61.7%) | 3 | 38 (66.7%) | 0.57 |
| Having pets from birth to enrollment | 2 | 15 (25.4%) | 7 | 6 (11.3%) | 0.088 |
| Smoking in the household | 3 | 12 (20.7%) | 4 | 14 (25.0%) | 0.66 |
| Hen's egg elimination by mother during lactation at baseline | 4 | 15 (26.3%) | 1 | 15 (25.4%) | 1.00 |
| Continuation of lactation | | | | | |
| at 6 month of age | 1 | 56 (93.3%) | 0 | 57 (95.0%) | 0.70 |
| at 12 month of age | 2 | 43 (72.9%) | 3 | 37 (64.9%) | 0.35 |

Comparing both groups by Fisher's exact test

FIG. 13

Table E3. Details of Baseline Characteristics

| Characteristic | Placebo group (N=61) | | | | | | Egg group (N=60) | | | | | | P value |
|---|---|---|---|---|---|---|---|---|---|---|---|---|---|
| | Missing value | Mean | SD | Median | 25% | 75% | Missing value | Mean | SD | Median | 25% | 75% | |
| Age at enrollment (day) | 0 | 163·4 | 19·9 | 168 | 153 | 179 | 0 | 162·2 | 21·5 | 167·5 | 152 | 177·25 | 0·87 |
| Gestational age (weeks) | 9 | 39·1 | 1·3 | 39 | 38 | 40 | 4 | 38·9 | 1·2 | 39 | 38 | 40 | 0·44 |
| Birth weight (g) | 7 | 3108·3 | 325·4 | 3125 | 2841 | 3313 | 3 | 3162·8 | 373·8 | 3154 | 2934 | 3480 | 0·40 |
| Age at onset of eczema (mo) | 5 | 1·8 | 1·1 | 2 | 1 | 3 | 1 | 2·0 | 1·1 | 2 | 1 | 3 | 0·40 |
| SCORAD score | 1 | 36·1 | 21·0 | 42 | 22·1 | 52·3 | 2 | 28·3 | 20·3 | 27·5 | 10·3 | 38·2 | 0·030 |
| TARC (pg/mL) | 0 | 5133 | 6733 | 3165 | 1532 | 5867 | 0 | 3053 | 3340 | 2297 | 1525 | 3250 | 0·048 |
| Total IgE (IU/mL) | 4 | 146·8 | 232·2 | 41·2 | 15·9 | 181 | 3 | 46·5 | 110·3 | 16·5 | 5·3 | 51·2 | 0·00024 |
| Egg white-specific IgE (kUA/L) | 3 | 16·21 | 25·02 | 4·46 | 0·47 | 24·83 | 3 | 5·89 | 11·90 | 0·73 | 0·17 | 5·55 | 0·0051 |
| Ovomucoid-specific IgE (kUA/L) | 5 | 3·04 | 7·63 | 0·35 | 0·17 | 0·56 | 8 | 0·98 | 2·55 | 0·17 | 0·17 | 0·35 | 0·051 |
| Age at start of solid foods (mo) | 3 | 5·6 | 0·7 | 6 | 5 | 6 | 2 | 5·6 | 0·7 | 6 | 5 | 6 | 0·92 |
| POEM at 6 months of age | 7 | 2·9 | 3·2 | 2 | 0·3 | 4 | 8 | 2·1 | 2·8 | 1 | 0 | 2·3 | 0·15 |

Comparing both groups by Wilcoxon rank-sum tests· SCORAD=Scoring atopic dermatitis· TARC=Thymus and activation-regulated chemokine· POEM=Patient-Oriented Eczema Measure·

FIG. 14

Table E4. The details of participants who were positive in oral food challenge to heated whole egg at 12 months of age.

| No. | Allocation | Cumulative egg powder dose† at first symptom (g) | Symptoms | Medication | Total IgE at 12 months (IU/mL) | Egg white-specific IgE at 12 months (kUA/L) | Ovomucoid-specific IgE at 12 months (kUA/L) |
|---|---|---|---|---|---|---|---|
| 1 | EG | 7 | V | None | 125 | 22·9 | 6·32 |
| 2 | EG | 7 | PU | None | 108 | 16·7 | 4·69 |
| 3 | PG | 1 | SU, cough | Antihistamine | 731 | 100 | 18·1 |
| 4 | PG | 1 | SU | Antihistamine | 250 | 55·1 | 31·3 |
| 5 | PG | 3 | SU, V | Antihistamine | 423 | 57·1 | 90·5 |
| 6 | PG | 3 | PU | None | 86·2 | 9·98 | 0·11 |
| 7 | PG | 3 | SU | Antihistamine | 114 | 56·2 | 36·8 |
| 8 | PG | 3 | SU, wheeze | Antihistamine, salbutamol | 19·5 | 5·34 | 8·94 |
| 9 | PG | 4 | SU | Antihistamine×2 | 261 | 44·9 | 13 |
| 10 | PG | 6 | SU, rash around mouth | Antihistamine | 118 | 40·9 | 21·1 |
| 11 | PG | 7 | PU | Antihistamine | 53·5 | 5·16 | 0·17 |
| 12 | PG | 7 | PU | None | 20·6 | 2·31 | 1·91 |
| 13 | PG | 7 | Partial rash, continuous cough | Salbutamol | 452 | 29·6 | 26·2 |
| 14 | PG | 7 | V, diarrhea | None | 4797 | 100 | 100 |
| 15 | PG | 7 | PU | None | 57·8 | 10·2 | 0·17 |
| 16 | PG | 7 | SU | Antihistamine | 131 | 16·8 | 13·8 |
| 17 | PG | 7 | SU | Antihistamine | 116 | 29·8 | 20·7 |
| 18 | PG | 7 | SU | Antihistamine | 29·7 | 6·05 | 8·99 |
| 19 | PG | 7 | PU | None | 44·9 | 4·72 | 6·55 |
| 20 | PG | 7 | SU | Antihistamine×2 | 96·8 | 6·98 | 4·01 |
| 21 | PG | 7 | SU | Antihistamine | 107 | 14·7 | 3·54 |
| 22* | PG | 1 | SU, V, hypotension | Antihistamine, adrenaline | 144 | 25·6 | 10·9 |
| 23* | PG | 7 | SU | Antihistamine | 13·6 | 2·06 | 1·04 |
| 24* | PG | 7 | SU | None | 104 | 19·4 | 5·6 |

EG, egg group; PG, placebo group; PU, partial urticaria; SU, systemic urticaria; V, vomiting
*Excluded from per-protocol analysis because they took the trial powder for less than 130 days; †Seven g of heated whole egg powder is equivalent to 32 g of boiled egg.

FIG. 15

Table E5. Adjusted analysis of primary outcome by the logistic regression model

| | Factor of adjustment for primary outcome | Odds ratio (95% CI) | P value |
|---|---|---|---|
| ITT | None (crude) | 0·150 (0·052-0·430) | 0·0002 |
| | SCORAD* | 0·113 (0·035-0·361) | 0·0002 |
| | History of father and mother | 0·161 (0·056-0·468) | 0·0008 |
| | Start of solid foods (mo) | 0·083 (0·023-0·297) | 0·0001 |
| | SCORAD*, allergic history of father and mother, start of solid foods (mo) | 0·087 (0·024-0·322) | 0·0003 |
| | Gender | 0·149 (0·052-0·428) | 0·0004 |
| | TARC* | 0·156 (0·054-0·451) | 0·0006 |
| | Log total IgE† | 0·206 (0·068-0·622) | 0·0051 |
| | Log Egg White-sIgE† | 0·189 (0·063-0·565) | 0·0029 |
| | POEM ‡ | 0·063 (0·014-0·287) | 0·0004 |
| | SCORAD* and log Egg white-sIgE† | 0·131 (0·039-0·446) | 0·0012 |
| | SCORAD*, log Egg white-sIgE†, allergic history of father and mother, start of solid foods (mo) and POEM ‡ | 0·076 (0·014-0·408) | 0·0026 |
| PPA | None (crude) | 0·074 (0·016-0·342) | <0·0001 |
| | SCORAD* | 0·080 (0·017-0·376) | 0·0014 |
| | History of father and mother | 0·084 (0·018-0·393) | 0·0017 |
| | Start of solid foods (mo) | 0·069 (0·015-0·320) | 0·0006 |
| | SCORAD*, allergic history of father and mother, start of solid foods (mo) | 0·087 (0·018-0·411) | 0·0021 |
| | Gender | 0·074 (0·016-0·342) | 0·0009 |
| | TARC* | 0·078 (0·016-0·369) | 0·0013 |
| | Log total IgE† | 0·107 (0·022-0·518) | 0·0055 |
| | Log egg white-specific IgE† | 0·083 (0·017-0·404) | 0·0021 |
| | POEM ‡ | 0·080 (0·017-0·372) | 0·0013 |
| | SCORAD* and log egg white-specific IgE† | 0·082 (0·016-0·419) | 0·0026 |
| | SCORAD*, log egg white-specific IgE†, allergy history of father and mother, start of solid foods (mo) and POEM** | 0·098 (0·018-0·533) | 0·0072 |

ITT, intention-to-treat analysis; PPA, per-protocol analysis; SCORAD, Scoring atopic dermatitis; POEM, Patient-Oriented Eczema Measure· *evaluated at first visit; †evaluated at enrollment; **average during intervention (6 to 12 months of age)

Table E6. Secondary outcome

| | Egg group | Placebo group | P value | | Egg group | Placebo group | P value |
|---|---|---|---|---|---|---|---|
| Egg white-specific IgE (kUA/L) | | | | Ovomucoid-specific IgE | | | |
| 4 to 5 months of age | 0·73 (0·17-5·55) | 4·46 (0·47-24·83) | 0·0051 | 4 to 5 months of age | 0·17 (0·17-0·35) | 0·35 (0·17-0·56) | 0·051 |
| 9 months of age | 1·87 (0·46-7·61) | 6·04 (2·84-22·00) | 0·0003 | 9 moonths of age | 0·47 (0·17-1·51) | 0·17 (0·17-2·78) | 0·86 |
| 12 months of age | 1·62 (0·17-4·67) | 5·70 (2·30-25·78) | <0·0001 | 12 months of age | 0·17 (0·17-1·68) | 1·05 (0·17-5·84) | 0·025 |
| Egg white-specific IgG1 (BUg1/mL) | | | | Ovomucoid-specific IgG1 (BUg1/mL) | | | |
| 4 to 5 months of age | 1392·94 (150·43-4196·76) | 2074·97 (274·87-4424·75) | 0·28 | 4 to 5 months of age | 125·05 (101·94-198·97) | 150·20 (110·89-273·57) | 0·18 |
| 9 months of age | 4477·97 (3374·49-5852·59) | 4001·61 (2196·50-5480·49) | 0·36 | 9 months of age | 564·66 (258·83-3233·34) | 175·57 (109·76-888·39) | 0·0002 |
| 12 months of age | 4896·63 (4227·33-5781·54) | 5033·92 (3337·28-6251·88) | 0·77 | 12 months of age | 2132·01 (1294·82-4611·93) | 603·97 (148·25-2292·46) | <0·0001 |
| Egg white-specific IgG4 (BUg4/mL) | | | | Ovomucoid-specific IgG4 (BUg4/mL) | | | |
| 4 to 5 months of age | 50·00 (50·00-58·17) | 52·55 (50·00-59·16) | 0·22 | 4 to 5 months of age | 50·00 (50·00-51·69) | 50·00 (50·00-51·28) | 0·82 |
| 9 months of age | 51·21 (50·00-54·75) | 52·80 (50·00-63·73) | 0·033 | 9 months of age | 50·00 (50·00-60·88) | 50·00 (50·00-50·73) | 0·18 |
| 12 months of age | 54·71 (50·00-67·93) | 62·22 (50·38-93·10) | 0·30 | 12 months of age | 57·05 (50·00-102·39) | 50·00 (50·00-63·27) | 0·0087 |
| Egg white-specific IgA (BUA/mL) | | | | Ovomucoid-specific IgA (BUA/mL) | | | |
| 4 to 5 months of age | 4·73 (3·37-8·66) | 5·03 (3·59-9·60) | 0·75 | 4 to 5 months of age | 2·50 (2·50-2·88) | 2·51 (2·50-2·94) | 0·47 |
| 9 months of age | 27·15 (16·21-45·65) | 7·83 (4·26-14·23) | <0·0001 | 9 months of age | 2·50 (2·50-7·56) | 2·50 (2·50-2·50) | 0·0021 |
| 12 months of age | 42·66 (16·75-88·64) | 10·42 (5·36-23·67) | <0·0001 | 12 months of age | 5·77 (2·62-11·33) | 2·50 (2·50-3·97) | 0·0001 |

Median (IQR)· Comparing both groups by Wilcoxon rank-sum tests·

Table E7. Specific IgE and IgG4 at 12 months of age in placebo group

|  | Placebo group | | P value |
|---|---|---|---|
|  | Without egg allergy | With egg allergy |  |
| Egg white-sIgE | 3.75 (2.02 -15.15) | 18.1 (5.87-47.45) | 0.0009 |
| Egg white-sIgG4 | 65.18 (50.57-86.46) | 54.27 (50.00-113.6) | 0.71 |
| Ovomucoid-sIgE | 0.59 (0.10-2.43) | 9.95 (3.13-22.38) | <0.0001 |
| Ovomucoid IgG4 | 50.00 (50.00-52.94) | 60.66 (50.00-83.47) | 0.0039 |

Median (IQR). Comparing by Wilcoxon rank-sum tests.

METHOD AND COMPOSITION FOR PREVENTING EGG ALLERGY

This Nonprovisional application claims priority under U.S.C. § 119 on Provisional Patent Application No. 62/451,671 filed in USPTO on Jan. 28, 2017, the entire contents of which are hereby incorporated by reference.

TECHNICAL FIELD

The present invention relates to method and composition for preventing egg allergy.

BACKGROUND ART

A second wave of the allergy epidemic, in the form of a rising prevalence of food allergies, has emerged in high-income countries following the first wave of increasing asthma and allergic rhinitis [Non patent literature 1]. Food allergy often occurs in the early stage of the allergic march [Non patent literature 2], along with atopic dermatitis, and is associated with increased risks of anaphylaxis and asthma [Non patent literature 3]. Hen's egg allergy is one of the commonest forms of food allergy, with sensitisation to egg at 1 year of age strongly associated with sensitisation to aeroallergens at years of age [Non patent literature 4]. Although food allergy and atopic dermatitis (and subsequent asthma) have been widely believed to be prevented by avoidance of specific food during the perinatal and infancy periods [Non patent literatures 5, 6], such an approach has not been supported by a Cochrane systematic review [Non patent literatures 7].

CITATION LIST

Non-Patent Literature

1 Prescott S, Allen K J. Food allergy: riding the second wave of the allergy epidemic. *Pediatr Allergy Immunol* 2011; 22: 155-60.

2 Wong G W. Epidemiology: international point of view, from childhood to adults, food allergens. *Chem Immunol Allergy* 2015; 101: 30-37.

3 Schroeder A, Kumar R, Pongracic J A, et al. Food allergy is associated with an increased risk of asthma. *Clin Exp Allergy* 2009; 39: 261-70.

4 Dean T, Venter C, Pereira B, et al. Patterns of sensitization to food and aeroallergens in the first 3 years of life. *J Allergy Clin Immunol* 2007; 120: 1166-71.

5 American Academy of Pediatrics. Committee on Nutrition. Hypoallergenic infant formulas. *Pediatrics* 2000; 106: 316-49.

6 Fiocchi A, Assa'ad A, Bahna S. Food allergy and the introduction of solid foods to infants: a consensus document. Adverse Reactions to Foods Committee, American College of Allergy, Asthma and Immunology. *Ann. Allergy Asthma Immunol* 2006; 97: 10-20.

7 Kramer M S, Kakuma R. Maternal dietary antigen avoidance during pregnancy or lactation, or both, for preventing or treating atopic disease in the child. *Cochrane Database Syst Rev* 2012; 9: CD000133.

8 Koplin J J, Osborne N J, Wake M, et al. Can early introduction of egg prevent egg allergy in infants? A population-based study. *J Allergy Clin Immunol* 2010; 126: 807-13.

9 Katz Y, Rajuan N, Goldberg M R, et al. Early exposure to cow's milk protein is protective against IgE-mediated cow's milk protein allergy. *J Allergy Clin Immunol* 2010; 126: 77-82.e1.

10 Roduit C, Frei R, Depner M, et al. Increased food diversity in the first year of life is inversely associated with allergic diseases. *J Allergy Clin Immunol* 2014; 133: 1056-64.

11 Kull I, Bergstrom A, Lilja G, Pershagen G, Wickman M. Fish consumption during the first year of life and development of allergic diseases during childhood. *Allergy* 2006; 61: 1009-15.

12 Du Toit G, Roberts G, Sayre P H, et al. Randomized trial of peanut consumption in infants at risk for peanut allergy. *N Engl J Med* 2015; 372: 803-13.

13 Palmer D J, Metcalfe J, Makrides M, et al. Early regular egg exposure in infants with eczema: a randomized controlled trial. *J Allergy Clin Immunol* 2013; 132: 387-92.e1.

14 Perkin M R, Logan K, Tseng A, et al. Randomized trial of introduction of allergenic foods in breast-fed infants. *N Engl J Med* 2016; 374: 1733-43.

15 Lack G. Epidemiologic risks for food allergy. *J Allergy Clin Immunol* 2008; 121: 1331-36.

16 Brough H A, Liu A H, Sicherer S, et al. Atopic dermatitis increases the effect of exposure to peanut antigen in dust on peanut sensitization and likely peanut allergy. *J Allergy Clin Immunol* 2015; 135: 164-70.

17 Lack G, Fox D, Northstone K, Golding J. Factors associated with the development of peanut allergy in childhood. *N Engl J Med* 2003; 348: 977-85.

18 Hanifin J M, Rajka. G. Diagnostic features of atopic dermatitis. *Acta Derm Venereal (Stockh)* 1980; 92 (suppl): 44-47.

19 Fukuie T, Nomura I, Horimukai K., et al. Proactive treatment appears to decrease serum immunoglobulin-E levels in patients with severe atopic dermatitis. *Br J Dermatol* 2010; 163: 1127-29.

20 Suzuki K, Hiyoshi M, Tada H, et al. Allergen diagnosis microarray with high-density immobilization capacity using diamond-like carbon-coated chips for profiling allergen-specific IgE and other immunoglobulins. *Anal Chim Acta* 2011; 706: 321-27.

21 Severity scoring of atopic dermatitis: the SCORAD index. Consensus Report of the European Task Force on Atopic Dermatitis. *Dermatology* 1993; 186: 23-31.

22 Charman C R, Venn A J, Williams H C. The patient-oriented eczema measure: development and initial validation of a new tool for measuring atopic eczema severity from the patients' perspective. *Arch Dermatol* 2004; 140: 1513-19.

23 Ito K, Morishita M, Ito A, Sakamoto T, Torii S. [Immediate type food hypersensitivity associated with atopic dermatitis in children]. *Arerugi* 2004; 53: 24-33 (in Japanese).

24 Hamasaki Y, Kohno Y, Ebisawa M, et al. Japanese Guideline for Childhood Asthma 2014. *Allergol Int* 2014; 63: 335-56.

25 Nakamura Y, Yashiro M, Uehara R, et al. Epidemiologic features of Kawasaki disease in Japan: results of the 2009-2010 nationwide survey. *J Epidemiol* 2012; 22: 216-21.

26 e-Stat Portal Site of Official Statistics in Japan. Patients statistics in Japan 2016. http://www.estat.go.jp/SG1/estat/GL080201.03.do?_toG L08020103_&listID=000001141-596&requestSender=dsearch (accessed Feb. 2, 2016).

27 Flohr C, Perkin M, Logan K, et al. Atopic dermatitis and disease severity are the main risk factors for food sensitization in exclusively breastfed infants. *J Invest Dermatol* 2014; 134: 345-50.

28 Hill D J, Hosking C S, de Benedictis F M, Oranje A P, Diepgen T L, Bauchau V. Confirmation of the association between high levels of immunoglobulin E food sensitization and eczema in infancy: an international study. *Clin Exp Allergy* 2008; 38: 161-68.

SUMMARY OF INVENTION

Technical Problem

Conversely, findings from observational studies [Non patent literatures 8-11] have revealed that early introduction of solid food might decrease the incidence of food allergy compared with late introduction or avoidance. Several randomised controlled trials (RCTs) have been done to test the possible protective role of early introduction of solid foods. Investigators of the Learning Early About Peanut (LEAP) study [Non patent literature 12] investigated the effect of introduction of peanuts in high-risk infants and found that early introduction reduced the prevalence of peanut allergy at 5 years of age (relative risk 0.19; p<0.0001). Results of another RCT [Non patent literature 13] that investigated the effect of egg introduction at 4 months of age did not show any protection (relative risk of hen's egg allergy at 12 months 0.65; p=0.11) and highlighted a major problem of such an approach in infants with moderate-to-severe eczema because many might have sensitisation and clinical reactivity to egg by 4 months of age. In both RCTs, a considerable number of participants had allergic reactions to several types of food at first introduction. The Enquiring About Tolerance study [Non patent literature 14] assessed the possible preventive effect of early introduction of six types of food, including peanuts and hen's eggs, in infants from the general population. The complex protocol had rather low adherence and the results in the intention-to-treat analysis were negative. Findings of these RCTs suggest that a safe and practical approach for introduction of allergenic foods to high-risk infants with eczema is still very much needed.

The present invention was made in order to solve the foregoing problem, and an object of the present invention is to provide new method and composition for preventing egg allergy.

Solution to Problem

In order to solve the foregoing problems, an aspect of the present invention provides:
1) An egg allergy prevention method to be carried out with respect to a human infant, including:
a first administration period (first administration step) in which to administer, to an infant, heated egg white protein in an amount of 10 mg to 20 mg per day; and
a second administration period (second administration step) which is a period after the first administration period and in which to administer, to the infant, the heated egg white protein in an amount of 65 mg to 90 mg per day.
2) The egg allergy prevention method mentioned in 1), wherein:
in the first administration period, the heated whole egg protein is administered to the infant in an amount of 20 mg to 30 mg per day; and
in the second administration period, the heated whole egg protein is administered to the infant in an amount of 110 mg to 140 mg per day.
3) The egg allergy prevention method mentioned in 1), wherein:
in the first administration period, dry powder of heated whole egg or a composition containing the dry powder is administered to the infant in an amount of 40 mg to 60 mg of the dry powder per day; and
in the second administration period, the dry powder of the heated whole egg or the composition containing the dry powder is administered to the infant in an amount of 220 mg to 280 mg of the dry powder per day.
4) The egg allergy prevention method mentioned in 1), wherein:
in the first administration period, heated whole egg or a composition containing the whole egg is administered to the infant in an amount of 0.15 g to 0.25 g of the heated whole egg per day; and
in the second administration period, the heated whole egg or the composition containing the whole egg is administered to the infant in an amount of 0.88 g to 1.25 g of the heated whole egg per day.
5) The egg allergy prevention method mentioned in 1), wherein:
in the first administration period, dry powder of the heated egg white or a composition containing the dry powder is administered to the infant in an amount of 11 mg to 23 mg of the dry powder per day; and
in the second administration period, the dry powder of the heated egg white or the composition containing the dry powder is administered to the infant in an amount of 75 mg to 104 mg of the dry powder per day.
6) The egg allergy prevention method mentioned in 1), wherein the first administration period is 2 or more consecutive months selected from a period from 4 months to less than 10 months of age of the infant.
7) The egg allergy prevention method mentioned in 1), wherein the second administration period is 2 or more consecutive months selected from a period from 8 months to not more than 12 months of age of the infant.
8) The egg allergy prevention method mentioned in 1), wherein the egg allergy prevention method is to be carried out with respect to the infant who has eczema or has a history of eczema.
9) The egg allergy prevention method mentioned in 1), wherein the heated egg white protein is orally administered to the infant.
10) The egg allergy prevention method mentioned in 1), further including:
a further administration period (further administration step) which is different from each of the first administration period and the second administration period and which is between the first administration period and the second administration period,
in the further administration period, the egg white protein being administered to the infant in a greater amount per day than in an administration period followed by the further administration period, and in a smaller amount per day than in an administration period following the further administration period.
11) An egg allergy prevention composition to be administered to a human infant, containing:
heated egg white protein,
the heated egg white protein being administered in an amount of 10 mg to 20 mg per day.

12) An egg allergy prevention composition to be administered to a human infant, containing:
heated egg white protein,
the heated egg white protein being administered in an amount of 65 mg to 90 mg per day.

13) The egg allergy prevention composition mentioned in 11), wherein the egg allergy prevention composition contains the heated egg white protein in an amount of not more than 20 mg.

14) The egg allergy prevention composition mentioned in 12), wherein the egg allergy prevention composition contains the heated egg white protein in an amount of not more than 90 mg.

15) The egg allergy prevention composition mentioned in 11), wherein the egg allergy prevention composition contains the heated egg white protein in an amount of 2 mg to 20 mg.

16) The egg allergy prevention composition mentioned in 12), wherein the egg allergy prevention composition contains the heated egg white protein in an amount of 2 mg to 90 mg.

17) The egg allergy prevention composition mentioned in 11), wherein the egg allergy prevention composition is for use in oral administration.

18) The egg allergy prevention composition mentioned in 12), wherein the egg allergy prevention composition is for use in oral administration.

19) The egg allergy prevention composition mentioned in 11), wherein the egg allergy prevention composition contains the heated egg white protein in a form selected from the group consisting of a form of dry powder of heated whole egg, a form of dry powder of heated egg white, and a form of the heated whole egg or a processed product thereof.

20) The egg allergy prevention composition mentioned in 12), wherein the egg allergy prevention composition contains the heated egg white protein in a form selected from the group consisting of a form of dry powder of heated whole egg, a form of dry powder of heated egg white, and a form of the heated whole egg or a processed product thereof.

Topical Corticosteroid used: 0.1% Hydrocortisone butyrate ointment on face and neck, 0.12%

Betamethasone valerate ointment on trunks and extremities

Topical corticosteroids were applied until eczema disappeared and were used intermittently to maintain remission as shown in the figure. Remission was maintained with maximum of steroid applications 2 days a week for most of the participants.

Figure 7:
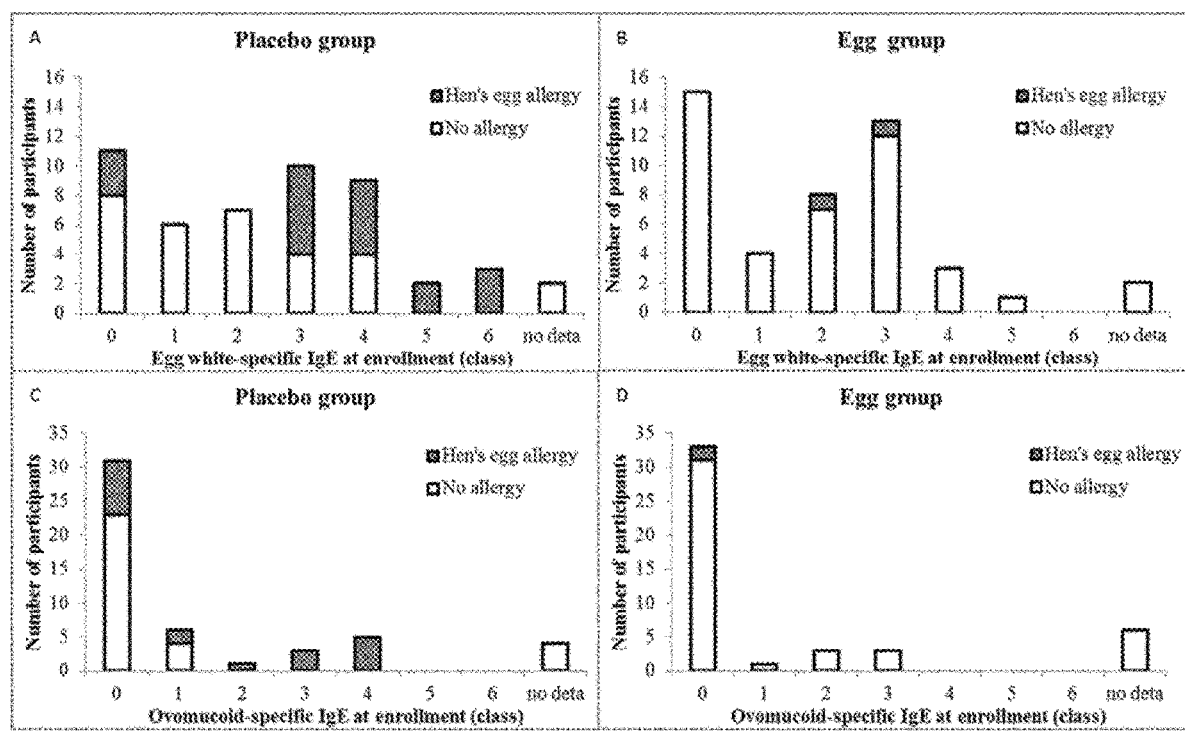

FIG. 7 relates to Primary outcome (hen's egg allergy at 12 months of age) stratified by serum egg-specific IgE at baseline (four to five months of age) in per-protocol population. (A) and (B) were stratified by the class of egg white-specific IgE at baseline (four to five months of age). (C) and (D) were stratified by the class of ovomucoid-specific IgE at baseline. Gray histograms indicate hen's egg allergy at 12 months of age.

Figure 8:
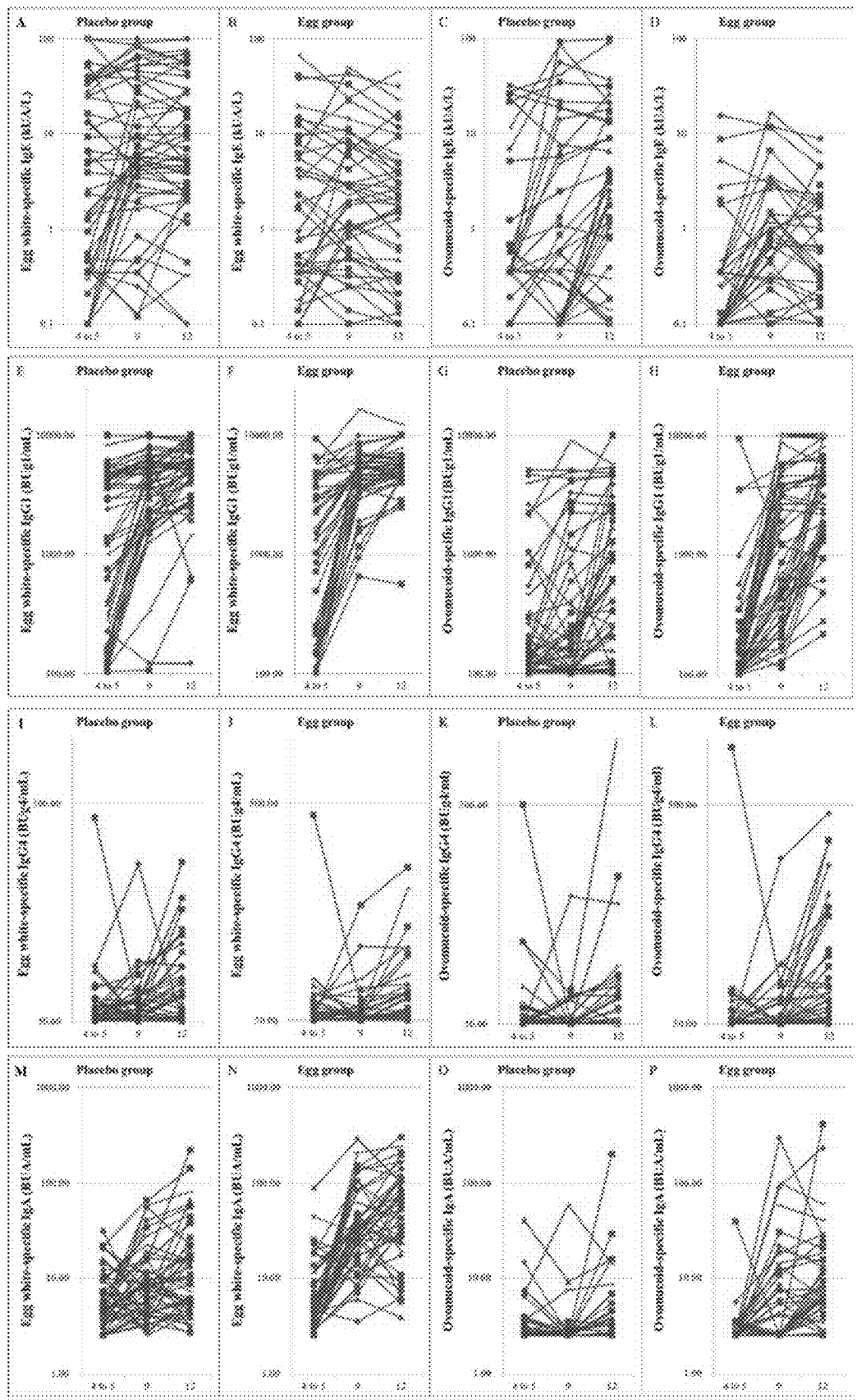

FIG. 8 relates to the sequential changes of individual specific IgE level. (A) and (B) shows the results of sequential changes of individual egg white-specific IgE level in the per protocol set population. (C) and (D) shows the changes of ovomucoid-specific IgE level in the same population. The results of IgG1 (E, F, G, H), IgG4 (I, J, K, L), and IgA (M, N, O, P) were shown similarly. Red lines represent the results of the participants with egg allergy at 12 months of age. Blue lines represent the result of the participants without egg allergy. Specific IgE was measured with immunoCAP (Thermo Fisher Scientific). Specific IgG1, IgG4, and IgA were measured with a recently established microarray system using DLC (diamond-like carbon)-coated densely carboxylated protein chips.

Figure 9:
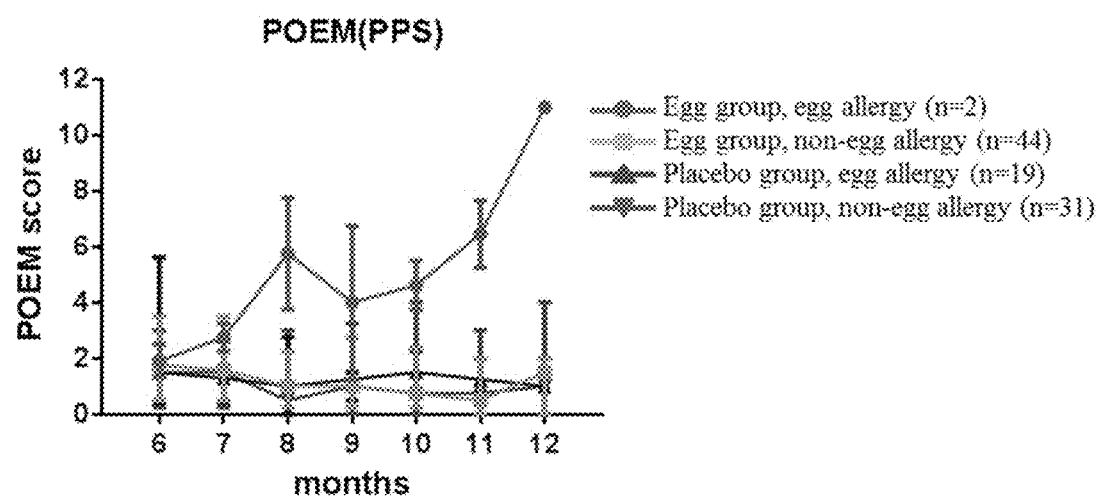

FIG. 9 relates to POEM scores of participants with or without egg allergy. Among the egg group, two Participants with egg allergy showed higher POEM score than the others between 6 and 12 months of age. Some participants in the placebo group developed egg allergy, although their POEM scores were low. Data are shown as the median and the 75th percentile. We used the mean POEM score during four weeks as the score of a particular month.

Figure 10:
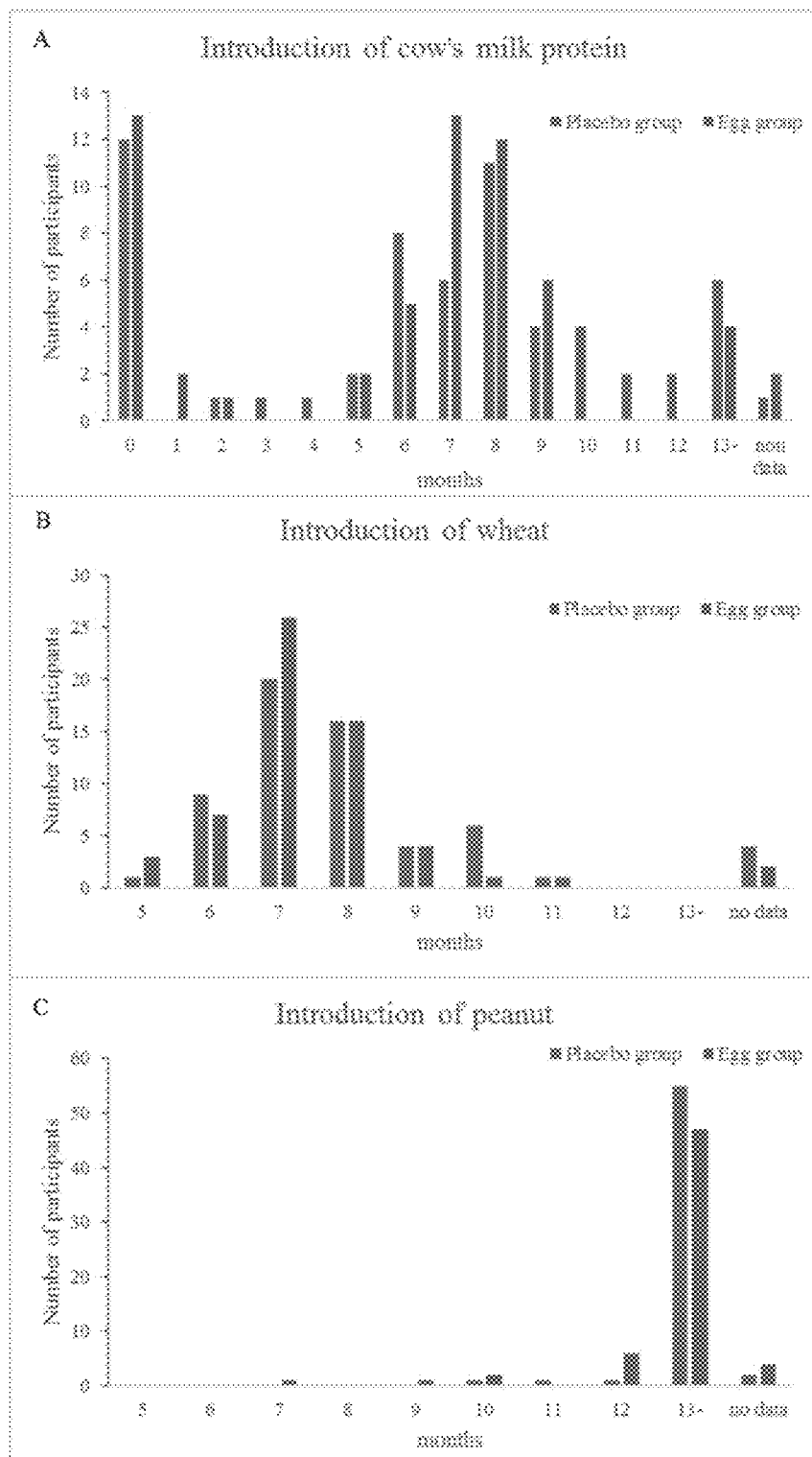

FIG. 10 relates to the timing of the other introduction. The timing of introduction of the solid foods other than hen's egg was evaluated by questionnaire at enrollment, 6, 9, 12 and 18 months of age. (A) Introduction of cow's milk protein was defined as continuous consumption of non-hydrolysed formula milk or dairy products. If a case was fed with non-hydrolysed formula milk until two months of age and started to eat dairy products from six months of age, the timing of introduction was defined as six month of age. (B) and (C) shows the timing of introduction of wheat and peanut, respectively.

FIG. 11 relates to Table E1. showing participants who withdrew from the trial.

FIG. 12 relates to Table E2. showing details of Baseline Characteristics.

FIG. 13 relates to Table E3. showing Details of Baseline Characteristics.

FIG. 14 relates to Table E4. showing the details of participants who were positive in oral food challenge to heated whole egg at 12 months of age.

FIG. 15 relates to Table E5. showing adjusted analysis of primary outcome by the logistic regression model.

FIG. 16 relates to Table E6. showing Secondary outcome.

FIG. 17 relates to Table E7. showing specific IgE and IgG4 at 12 months of age in placebo group.

DESCRIPTION OF EMBODIMENTS

The following will describe an embodiment of an aspect of the present invention in detail.

Term (Allergy)

An allergy is caused in a case where an allergen and immunoglobulin E (hereinafter, referred to as an "IgE antibody) each taken into a patient's body react with each other in the patient's body, stimulate a mast cell, and release inflammatory mediators such as histamine and leukotriene. More specifically, in a case where an allergen having passed through an alimentary canal mucosa and (b) respective Fab parts of two IgE, antibody molecules of IgE antibodies each of which (i) binds with a cell surface of a mast cell located at a spot which the allergen has entered and (ii) has an Fc part that binds with the cell surface bind together, and the two IgE antibody molecules crosslink with each other, a degranulatory response is produced in the mast cell. Histamine, leukotriene, serotonin, heparin, a slow-reacting substance (SRS-A), an eosinophilic chemotactic factor (ECF-A), and the like each contained in a granule of the mast cell are released, a series of immunopharmacological reactions such as smooth muscle contraction, supersecretion of mucus, and vascular hyperpermeability occurs, and an allergic symptom appears.

An allergic reaction is classified into type I through IV allergic reactions in accordance with, for example, a mechanism of tissue damage caused by an immune reaction. In particular, the type I allergic reaction, which is also called an "immediate reaction", occurs within several seconds to several hours after a contact with an allergen. Many of food allergies are classified as the type I allergic reaction.

A food allergy, which refers to an allergy that is caused by a food such as an egg, milk, a soybean, rice, or wheat, is an allergy that is caused by intake of such a food and/or an allergen contained in the food.

(Egg Allergy)

An egg allergy, which is a kind of food allergy, refers to an allergy that is caused by an allergen, which is protein contained in an egg.

(Egg)

An egg is a food containing a great amount of protein. Note that an egg herein refers to a hen's egg.

A structure of an egg is roughly divided into "shell", "yolk", and "egg white". "Egg white" is a part of an egg which part excludes shell and yolk. A "whole egg" herein refers to a whole of an egg except shell. "Egg white" contains much protein such as ovalbumin or ovomucoid. Such protein contained in egg white is known to relatively easily become an allergen and is also known to be made less allergenic by heat treatment.

According to an aspect of the present invention, "prevention" includes a reduction or a delay in future development of target illness in a subject who has not developed the target illness.

1. Egg Allergy Prevention Method

An aspect of the present invention provides an egg allergy prevention method to be carried out with respect to a human infant, including: a first administration period (first administration step) in which to administer, to an infant, heated egg white protein in an amount of 10 mg to 20 mg per day; and a second administration period (second administration step) which is a period after the first administration period and in which to administer, to the infant, the heated egg white protein in an amount of 65 mg to 90 mg per day.

According to an embodiment, the heated egg white protein is administered in an amount preferably of 12 mg to 19 mg in the first administration period, and the heated egg white protein is administered in an amount preferably of 67 mg to 86 mg in the second administration period.

Note that 10 mg to 20 mg of the egg white protein is equivalent to 16 mg to 32 mg of the heated whole egg protein, equivalent to 32 mg to 65 mg of dry powder of heated whole egg, equivalent to 11 mg to 23 mg of dry powder of heated egg white), or equivalent to 0.13 g to 0.26 g of the heated whole egg.

Note also that 12 mg to 19 mg of the egg white protein is equivalent to 20 mg to 30 mg of the heated whole egg protein, equivalent to 40 mg to 60 mg of dry powder of heated whole egg, equivalent to 14 mg to 22 mg of dry powder of heated egg white, or equivalent to 0.15 g to 0.25 g of the heated whole egg.

Note also that 65 mg to 90 mg of the egg white protein is equivalent to 105 mg to 147 mg of the heated whole e g protein, equivalent to 210 mg to 294 mg of dry powder of heated whole egg, equivalent to 75 mg to 104 mg of dry powder of heated egg white, or equivalent to 0.84 g to 1.3 g of the heated whole egg.

Note also that 67 mg to 86 mg of the egg white protein is equivalent to 110 mg to 140 mg of the heated whole egg protein, equivalent to 220 mg to 280 mg of dry powder of heated whole egg, equivalent to 77 mg to 100 mg of dry powder of heated egg white, or equivalent to 0.88 g to 1.25 g of the heated whole egg.

The above equivalents can be calculated based on respective proportions of ingredients of an egg which ingredients are listed in a known ingredient table. (e.g., 2015 STANDARD TABLES OF FOOD COMPOSITION IN JAPAN, Seventh Revised Edition)

The egg allergy prevention method of an embodiment is arranged such that:

the heated egg white protein is in a form of the heated whole egg protein;

in the first administration period, the heated whole egg protein is administered to the infant in an amount of 20 mg to 30 mg per day; and in the second administration period, the heated whole egg protein is administered to the infant in an amount of 110 mg to 140 mg per day.

The egg allergy prevention method of a further embodiment is arranged such that:

the heated egg white protein is in a form of dry powder of the heated whole egg or a composition containing the dry powder;

in the first administration period, dry powder of heated whole egg or a composition containing the dry powder is administered to the infant in an amount of 40 mg to 60 mg of the dry powder per day; and in the second administration period, the dry powder of the heated whole egg or the composition containing the dry powder is administered to the infant in an amount of 220 mg to 280 mg of the dry powder per day.

The egg allergy prevention method of a further embodiment is arranged such that:

the heated egg white protein is in a form of the heated whole egg or a composition containing the heated whole egg;

in the first administration period, heated whole egg or a composition containing the whole egg is administered to the infant in an amount of 0.15 g to 0.25 g of the heated whole egg per day; and in the second administration period, the heated whole egg or the composition containing the whole egg is administered to the infant in an amount of 0.88 g to 1.25 g of the heated whole egg per day.

The egg allergy prevention method of a further embodiment is arranged such that:

the heated egg white protein is in a form of dry powder of the heated egg white or a composition containing the dry powder;

in the first administration period, the dry powder of the heated egg white or the composition containing the dry powder is administered to the infant in an amount of 11 mg to 23 mg of the dry powder per day; and in the second administration period, the dry powder of the heated egg white or the composition containing the dry powder is administered to the infant in an amount of 75 mg to 104 mg of the dry powder per day.

(Heated Egg)

A "heated egg" herein refers to an egg that has been subjected to heat treatment. The heat treatment is carried out at a temperature at which protein contained in the egg is sufficiently denatured and for a duration for which the protein contained in the egg is sufficiently denatured. The "heated egg" is, for example, an egg that has been heated in boiling water for not less than 15 minutes, or an egg that has been heated at a temperature of not less than 60° C., not less than 63° C., not less than 65° C., not less than 75° C., not less than 80° C., or not less than 100° C. and not more than 120° C. for not less than 10 minutes, not less than 15 minutes, not less than 20 minutes, or not less than 30 minutes and not more than 60 minutes. Such an egg is herein also referred to as a "hard-boiled egg". Note that the heating can also be carried out by use of a spray dryer for use in drying (described later). In a case where an egg is thus sufficiently heated, protein contained therein can be made less allergenic. This further enhances safety.

"Heated egg white protein" herein refers to protein contained in heated egg white, and "heated whole egg protein" herein refers to protein contained in heated whole egg.

"Dry powder of heated whole egg" is obtained in a case where the heated whole egg is dried so as to be powderized, and "dry powder of heated egg white" is obtained in a case where the heated egg white is dried so as to be powderized.

Dry powder of heated whole egg herein refers to powder of heated whole egg which powder is obtained by drying the heated whole egg so that the powder has a residual water content of 4% by weight to 6% by weight.

Dry powder of heated egg white herein refers to powder of heated egg white which powder is obtained by drying the heated egg white so that the powder has a residual water content of 6% by weight to 9.5% by weight.

The above egg only needs to be dried by, for example, a hot air drying method, a spray drying method, a vacuum drying method, a freeze drying method, or a combination of these methods. Further, the above egg can also be sterilized or disinfected after or before being dried.

The dried egg is powderized by use of, for example, a powderizing device. Further, in order to make powder thus obtained uniform, it is also possible to add an operation such as sieving after powderization.

Dry powder of heated whole egg or dry powder of heated egg white of an embodiment is obtained by heating an egg at a temperature of not less than 60° C., not less than 63° C., not less than 65° C., not less than 75° C., not less than 80° C., or not less than 100° C. and not more than 120° C. for not less than 10 minutes, not less than 15 minutes, not less than 20 minutes, or not less than 30 minutes and not more than 60 minutes, and drying the egg by a preferable method of the drying methods mentioned above.

Alternatively, dry powder of heated whole egg or dry powder of heated egg white of a further embodiment can be obtained by simultaneously heating and drying an egg by spray drying.

Dry powder of heated whole egg of an example is obtained by heating an egg at a temperature of 63° C. for not less than 30 minutes and then spray-drying the egg (a condition under which to prepare frozen cooked egg powder (Kewpie Corporation, JAPAN)) used in Example).

For example, dry powder of heated whole egg for use in an aspect of the present invention contains 5.3% by weight of water and 50.4% by weight of whole egg protein (the contained amounts of these ingredients are identical to those of dry powder of heated whole egg (frozen cooked e g powder (Kewpie Corporation, JAPAN)) used in Examples (described later).

For example, dry powder of heated whole egg for use in an aspect of the present invention contains 4.5% by weight of water and 49.1% by weight of whole egg protein (2015, STANDARD TABLES OF FOOD COMPOSITION IN JAPAN, Seventh Revised Edition).

For example, dry powder of heated egg white for use in an aspect of the present invention contains 7.1% by weight of water and 86.5% by weight of egg white protein (2015, STANDARD TABLES OF FOOD COMPOSITION IN JAPAN, Seventh Revised Edition).

In addition, a form of heated egg white protein which egg white protein is to be administered is not limited to the form of dry powder. The egg white protein can be in a form of protein per se, or can be administered in a form of a composition. A specific form of the composition is described later in [2. Egg allergy prevention composition].

(Administration Target)

A prevention method in accordance with the present embodiment is applicable to a human infant. Further, an "infant" herein refers to an infant whose age is not more than 12 months (1 year old).

An infant as an administration target is preferably an infant who has never ingested egg protein, e.g., an infant who has not started eating egg white protein, egg yolk protein, whole egg protein, an egg, and an egg-containing product each of which is heated or unheated (i.e., an infant who has never eaten egg white protein, egg yolk protein, whole egg protein, an egg, and an egg-containing product each of which is heated or unheated.

It is preferable that during a period in which the egg allergy prevention method of an aspect of the present invention is carried out, an infant as an administration target is preferably prevented from ingesting, as, for example, meals, egg white protein, egg yolk protein, whole egg protein, an egg, and an egg-containing product each of which is heated or unheated, except heated egg white protein in any form to be administered in the present method.

(Symptom or Disease as Previous Illness Contracted by Administration Target, or Symptom or Disease Affecting Administration Target)

According to an embodiment, an administration target is a human infant who has at least one allergic symptom or is affected by at least one allergic disease (except an egg allergy), or a human infant who has at least one allergic symptom or has a history of at least one allergic disease (except an egg allergy).

Such an allergic disease is exemplified by but not limited to eczema (or infantile eczema), atopic dermatitis, allergic rhinitis, allergic conjunctivitis, allergic cystitis, pollinosis, a food (except an egg) allergy, anaphylaxis, bronchial asthma, and hives. Examples of an allergic symptom include itching of the mouth or an itchy eye, emesis, diarrhea, nasal discharge, headache, fever, and dermatitis.

Generally, as compared with an infant who has no allergic symptom or who is not affected by any allergic disease, an infant who has at least one allergic symptom or is affected by at least one allergic disease (except an egg allergy) as described above is more likely to develop an egg allergy, and can be said to have a higher risk of developing an egg allergy.

Further, an infant himself/herself who has no allergic symptom or who has no allergic disease and whose parent(s) or family member(s) has/have a hereditary predisposition to be easily affected by an allergic disease (e.g., has/have an allergic history) also has a higher risk of developing an egg allergy. Thus, such an infant is suitable as an administration target of an aspect of the present invention.

Thus, the administration target is, for example, the infant who has eczema or has a history of eczema. The infant who has atopic dermatitis or the infant who has developed eczema by 4 months of age or 5 months of age is also suitable as the administration target.

(Administration Amount)

In the first administration period, the heated egg white protein is administered per day in an amount preferably of 13.7 mg to 17.0 mg (equivalent to 22.5 mg to 27.5 mg of the heated whole egg protein, equivalent to 45 mg to 55 mg of dry powder of heated whole egg, equivalent to 15.5 mg to 20.0 mg of dry powder of heated egg white, or equivalent to 0.17 g to 0.23 g of the heated whole egg), more preferably of 14.7 mg to 16.0 mg (equivalent to 24 mg to 26 mg of the heated whole egg protein, equivalent to 48 mg to 52 mg of dry powder of heated whole egg, equivalent to 17.0 mg to 18.4 mg of dry powder of heated egg white, or equivalent to 0.18 g to 0.21 g of the heated whole egg), and still more preferably of 15.0 mg to 15.6 mg (equivalent to 24.5 mg to 25.5 mg of the heated whole egg protein, equivalent to 49 mg to 51 mg of dry powder of heated whole egg, equivalent to 17.3 mg to 18.1 mg of dry powder of heated egg white, or equivalent to 0.19 g to 0.20 g of the heated whole egg).

In the second administration period, the heated egg white protein is administered per day in an amount preferably of 73 mg to 80 mg (equivalent to 120 mg to 130 mg of the heated whole egg protein, equivalent to 210 mg to 260 mg of dry powder of heated whole egg, equivalent to 84 mg to 93 mg of dry powder of heated egg white, or equivalent to 0.96 g to 1.16 g of the heated whole egg), more preferably of 74 mg to 78 mg (equivalent to 122.5 mg to 127.5 m g of the heated whole egg protein, equivalent to 245 mg to 255 mg of dry powder of heated whole egg, equivalent to 85 mg to 91 mg of dry powder of heated egg white, or equivalent to 0.98 g to 1.14 g of the heated whole egg), and still more preferably of 75 mg to 77 mg (equivalent to 124 mg to 126 mg of the heated whole egg protein, equivalent to 248 mg to 252 mg of dry powder of heated whole egg, equivalent to 86 mg to 90 mg of dry powder of heated egg white, or equivalent to 0.99 g to 1.13 g of the heated whole egg).

(Timing of Administration, Administration Method, and Administration Period)

For example, an administration amount and an administration method can be appropriately selected in accordance with, for example, an age of a human infant as an administration target during an administration period, the infant's weight, sex of the infant, a formulation to be administered, and/or a degree of an intended effect of allergy prevention. The administration period can also be appropriately selected so that the intended effect of egg allergy prevention can be achieved. According to an embodiment, heated egg white protein is orally administered to the infant.

The first administration period is preferably 2 or more consecutive months, more preferably not less than 2 and not more than 4 consecutive months, and still more preferably not less than 2.5 and not more than 3.5 consecutive months, selected from preferably a period from 4 months to less than 10 months of age, and more preferably a period from 6 months to less than 9 months of age, of the infant.

The second administration period is preferably 2 or more consecutive months, more preferably not less than 2 and not more than 4 consecutive months, and still more preferably not less than 2.5 and not more than 3.5 consecutive months, selected from preferably a period from 8 months to not more than 12 months of age, and more preferably a period from 9 months to not more than 12 months of age, of the infant.

As a further embodiment, the egg allergy prevention method of an aspect of the present invention also includes a case where the heated egg white protein continues to be administered also after the second administration period. For example, the egg allergy prevention method of an aspect of the present invention also includes a case where the heated egg white protein continues to be administered also after the second administration period for a desired period and in a desired amount (e.g., under a condition identical to a condition under which the heated egg white protein is administered in the second administration period and in an amount identical to the amount in which the heated egg white protein is administered in the second administration period) and then the infant becomes more than 12 months of age when the administration is ended.

The heated egg white protein is administered preferably 1 time to 3 times, and more preferably 1 time to 2 times, per day. Assume that the heated egg white protein is administered 2 or more times per day. In this case, the heated egg white protein can be administered continuously or intermittently during a single day. In a case where the heated egg white protein is administered intermittently, the number of times of the administration and intervals at which to carry out the administration are not particularly limited. For example, the administration can be carried out 2 times: 1 time in the morning and 1 time in the evening. The heated egg white protein is administered to the infant on preferably not less than 70% of days, more preferably not less than 80% of the days, and still more preferably not less than 90% of the days, not less than 95% of the days, and 100% of the days (i.e., continuously every day), included in each of the first administration period and the second administration period.

The prevention method of a further embodiment further includes:

a further administration period (further administration step) which is different from each of the first administration period (first administration step) and the second administration period. (second administration step) and which is between the first administration period and the second administration period, in the further administration period (further administration step), the egg white protein being administered to the infant in a greater amount per day than in an administration period followed by the further administration period (e.g., the first administration period), and in a smaller amount per day than in an administration period following the further administration period (e.g., the second administration period). In this case, the further administration period can be one or more administration periods.

In the further administration period, the heated egg white protein is administered to the infant per day in an amount of, for example, 24 mg to 37 mg (equivalent to 40 mg to 60 mg of the heated whole egg protein, equivalent to 80 mg to 120 mg of dry powder of heated whole egg, equivalent to 28 mg to 43 mg of dry powder of heated egg white, or equivalent to 0.3 g to 0.5 g of the heated whole egg), more preferably of 27 mg to 34 mg (equivalent to 44 mg to 56 mg of the heated whole egg protein, equivalent to 90 mg to 110 mg of dry powder of heated whole egg, equivalent to 31 mg to 40 mg of dry powder of heated egg white, or equivalent to 0.33 g to 0.46 g of the heated whole egg).

Further, preceding and following administration periods (For example, the preceding and following administration periods are the first administration period and the second administration period. In a case where the further administration period is present, the preceding and following administration periods are the first administration period, the further administration period, and the second administration period) are preferably continuous with each other.

Specifically, it is preferable to carry out the administration as continuously as possible without providing a period in which the administration is suspended.

A schedule of the administration is exemplified by but not particularly limited to a schedule such that the first administration period is 6 months to 9 months of age of the infant and is followed by the second administration period, which is 9 months to 12 months of age of the infant.

(Inspection Step)

The prevention method in accordance with an aspect of the present invention can further include, as appropriate, an inspection step of inspecting the infant for development of an egg allergy.

The inspection is carried out by, for example, measurement of a specific IgE antibody titer or an eosinophilic value with a blood test, a skin test (prick test), or a food load test.

The inspection step is carried out at, for example, an end of each of the administration periods.

(Combination Therapy)

It is possible to carry out combination therapy by combining the egg allergy prevention method in accordance with an aspect of the present invention with egg allergy prevention different from an aspect of the present invention. In a case where combination therapy is carried out, a preventive effect that is synergistic with a preventive effect of a combination drug can be expected to be achieved.

In a case where an administration target is an infant who has, for example, atopic dermatitis, treatment for atopic dermatitis is preferably carried out in combination with egg allergy prevention of the present invention. Examples of the treatment for atopic dermatitis include administration of an antihistamine, an antiallergic drug, and/or a steroid, and application of a moisturizing agent for relief of a skin symptom.

It is known that though a healthy intestinal tract is highly active in inducing immunological tolerance, entry of an antigen into the intestinal tract from a skin with eczema causes development and exacerbation of an allergic disease. Thus, dermatitis which is left interferes with an effect of oral ingestion. Consequently, a state of a skin of the administration target is preferably kept good by carrying out treatment for eczema, atopic dermatitis, or the like in combination with egg allergy prevention of the present invention.

As described earlier, according to the egg allergy prevention method of an aspect of the present invention, a human infant who ingests heated egg white protein at an early stage of a weaning period can prevent development of an egg allergy.

2. Egg Allergy Prevention Composition

An aspect of The present invention provides an egg allergy prevention composition (a composition for egg allergy prevention) to be administered to a human infant, containing: heated egg white protein, the egg white protein being administered in an amount of 10 mg to 20 mg per day (this egg allergy prevention composition is referred to as a "composition (1)"). According to the composition (1), the heated egg white protein is administered in an amount preferably of 12 mg to 19 mg per day.

An aspect of The present invention provides an egg allergy prevention composition to be administered to a human infant, containing: heated egg white protein, the egg white protein being administered in an amount of 65 mg to 90 mg per day (this egg allergy prevention composition is referred to as a "composition (2)"). According to the composition (2), the heated egg white protein is administered in an amount preferably of 67 mg to 86 mg per day.

An example of the composition (1) contains the heated egg white protein in an amount of not more than 20 mg, e.g., in an amount of 2 mg to 20 mg. An example of the composition (2) contains the heated egg white protein in an amount of not more than 90 mg, e.g., in an amount of 2 mg to 90 mg.

According to an embodiment, the composition (1) can be applied in the first administration period of the egg allergy prevention method of an aspect of the present invention, and the composition (2) can be applied in the second administration period of the egg allergy prevention method of an aspect of the present invention.

For example, in a case where the heated egg white protein is administered to the infant in the above amount per day of not at a time but a plurality of times, an amount of the egg white protein which is contained in a composition administered each time can be adjusted so that a total amount of the heated egg white protein which egg white protein is contained in the composition administered each time is the above amount per day. The egg white protein contained in the composition administered each time can be either identical or different in amount.

(Application)

The above compositions or a combination thereof are applicable to prevention of an egg allergy. Such a composition, which is not limited in kind, is exemplified by medicinal compositions (also referred to as "pharmaceutical compositions") and food and drink compositions. A specific embodiment in each application is described later.

The egg allergy prevention composition (1) is preferably to be administered to the infant whose age is 4 months to 10 months, and preferably 6 months to 9 months.

The egg allergy prevention composition (2) is preferably to be administered to the infant whose age is 8 months to 12 months, and preferably 9 months to 12 months.

As a target to which to administer the compositions of an aspect of the present invention and a combination thereof, the administration target described in [1. Egg allergy prevention method] is employed.

The compositions (1) and (2) of an aspect of the present invention, and a combination thereof are applicable to the administration of the heated egg white protein in the egg allergy prevention method of an aspect of the present invention. The composition (1) or (2) of an embodiment is for use in oral administration.

A further example of the egg allergy prevention composition of an aspect of the present invention is an egg allergy prevention composition to be administered to a human infant, containing: heated egg white protein, the egg white protein being administered in an amount of 24 mg to 37 mg per day (this composition is referred to as a "composition (3)").

A further administration period which is different from each of the first administration period and the second administration period is between the first administration period and the second administration period, and the egg allergy prevention composition (3) can be administered to the infant in the further administration period.

The egg allergy prevention composition of an embodiment contains the heated egg white protein in a form selected from the group consisting of a form of dry powder of heated whole egg, a form of dry powder of heated egg white, and a form of the heated whole egg or a processed product thereof. Alternatively, the egg allergy prevention composition of an embodiment can contain the heated egg white protein in two or more of these forms.

The egg allergy prevention composition of an aspect of the present invention includes both a form of a medicinal composition and a form of a food and drink composition.

(Medicinal Composition (Pharmaceutical Composition) for Egg Allergy Prevention)

An embodiment of the above-described composition of the present invention is a medicinal composition for egg allergy prevention. The medicinal composition for egg allergy prevention is a composition that contains heated egg white protein as an active ingredient.

The medicinal composition of the present embodiment has a remarkable effect of egg allergy prevention. Thus, administration of such a medicinal product to a subject makes it possible to prevent an egg allergy. Consequently, the medicinal composition of the present embodiment is useful for, for example, a human infant who has a risk of developing an egg allergy (e.g., a human infant who is affected by atopic dermatitis).

As an embodiment, the medicinal composition of the present invention further contains at least one substance selected from, for example, a preferable solvent, a preferable carrier, other preferable ingredient such as a preferable diluting agent, and a preferable adjuvant. The following description discusses ingredients of the medicinal product. The medicinal composition of an aspect of the present invention can also contain a further publicly known agent for egg allergy suppression or an active ingredient having an effect different from egg allergy suppression, provided that such an agent or such an active ingredient does not inhibit an effect of the active ingredient of the medicinal composition of an aspect of the present invention.

(Solvent)

Examples of a solvent of the medicinal composition of an aspect of the present invention include water and a buffer solution. Examples of the buffer solution include physiological saline, a phosphate buffer solution, and a Ringer solution. Note that the solvent which is used in the medicinal composition can also be a mixture of two or more kinds of the above solvents.

(Other Ingredient(s))

Other ingredient(s) that is/are used in the medicinal product of an aspect of the present invention is/are exemplified by but not particularly limited to various desired substances each of which is publicly known as a material for a preparation. Such a substance is exemplified by but not particularly limited to a preserving agent, a stabilizing agent, a diluting agent, a lubricant, a binding agent, a disintegrating agent, a surfactant, and a filler. Further, preparation additives) such as an antiseptic agent, a coloring agent, a natural pigment, and/or a sweetening agent can also be used as appropriate. Examples of the other ingredient(s) include glucose and pumpkin powder.

(Formulation)

A formulation of the medicinal composition of an aspect of the present invention is exemplified by but not particularly limited to a liquid formulation, a solid formulation, a semisolid formulation, and a semiliquid formulation. Such a formulation can be easily produced by a person skilled in the art in accordance with a publicly known method. Examples of the liquid formulation include a preparation and a syrup each obtained by dispersing, suspending, or dissolving an active ingredient in accordance with an aspect of the present invention in a solvent so that the solvent contains the active ingredient. Examples of the solid formulation include powder, a granule, a tablet, and capsules (a hard capsule, a soft capsule, and a microcapsule). Examples of the semisolid formulation or the semiliquid formulation include an ointment, a lotion, a cream, gel, a suspension agent, and an emulsion.

The above medicinal compositions can be produced by use of a method that is commonly used in the field of preparation technology.

According to a further embodiment, the medicinal compositions can also be produced by adding a composition for egg allergy prevention of an aspect of the present invention to various publicly known medicinal compositions.

(Route of Administration)

A route by which to administer the medicinal composition of an aspect of the present invention is exemplified by but not limited to oral administration, local administration, subcutaneous administration, intramuscular administration, intravenous administration, intradermal administration, and transdermal administration. Above all, oral administration is preferable from the viewpoint of easiness of administration.

(Administration Method)

The medicinal composition of an aspect of the present invention is administered to a subject in accordance with a publicly known method such as injection directly under the skin, injection directly into a vein, injection directly into muscle, or injection directly into the abdominal cavity; spray into an intranasal mucous membrane, an intraoral mucous membrane, an intrapulmonary mucous membrane, an intravaginal mucous membrane, or an intrarectal mucous membrane; oral administration; or intravascular administration.

(Use Application)

The medicinal composition of an aspect of the present invention is specifically used to (i) prevent development of an egg allergy and (ii) prevent other disease(s), illness(es), or symptom(s) that may accompany development of an egg allergy.

For example, the medicinal composition of an aspect of the present invention can also be administered in combination with a further medicinal composition that has an effect of egg allergy suppression or has an effect different from egg allergy suppression, provided that the further medicinal composition does not impair an effect of egg allergy suppression of an agent for egg allergy suppression.

(Food and Drink Composition for Egg Allergy Prevention)

A composition in accordance with a further embodiment of the present invention is a food and drink composition. Examples of the food and drink composition include not only common foods and drinks (beverages, foodstuffs) but also supplements, foods and drinks for specified health use, foods and drinks with function claims, and foods and drinks with nutrient function claims.

These food and drink compositions (in particular, foods and drinks for specified health use, foods and drinks with function claims, foods and drinks with nutrient function claims, etc.) can display a function and efficacy of, for example, egg allergy prevention.

In a case where a "food and drink composition" of an aspect of the present invention is in a form of a preparation, the food and drink composition can be arranged as in the case of the medicinal composition. Specifically, the "food and drink composition" of an aspect of the present invention can be arranged such that (i) food and drink contains an agent for egg allergy suppression in an amount that is in accordance with an amount in which the medicinal composition contains the agent for egg allergy suppression and (ii) a formulation thereof, which is in accordance with that of the medicinal composition, is, for example, a tablet, a capsule, a health drink, or a dust formulation.

The food and drink composition in accordance with an aspect of the present invention prevents an egg allergy in a living organism by causing the living organism to orally ingest the food and drink composition. Thus, the food and drink composition is preferably in a form that is easy to orally ingest.

According to an aspect of the present invention, the food and drink composition can also contain ingredient(s) to be added to food and drink, such as a seasoning, an acidulant, a sweetener, a spice, a colorant, a flavor, a salt, a sugar, an antioxidant, a vitamin (e.g., vitamin C, vitamin A, vitamin E, etc.), a mineral (e.g., zinc, copper, manganese, etc.), a stabilizing agent, a thickening agent, a carrier, a diluting agent, a lubricant, a surfactant, a propellant, an antiseptic agent, a chelating agent, and/or a pH adjuster.

The food and drink composition is not particularly limited in form and can be in a form of, for example, a solid (a tablet, powder, a granule, or the like), a semisolid (e.g., a paste), a liquid (a solution, a suspension, an emulsion, or the like), or an encapsulation. The foods and drinks are exemplified by but not particularly limited in kind to weaning foods, seasoning liquids e.g., sauce and the like), noodles, meat products (e.g., ham, sausage, and the like), fish meat products (e.g., kamaboko (boiled fish paste chikuwa (tube-shaped fish paste cake), and the like), dairy products (e.g., butter, cheese, and the like), vegetable processed products, prepared foods, confectionery (e.g., biscuits, cookies, candies, snacks, ramunegashi (soda candies), and the like), beverages (e.g., a health drink, milk beverage, a coffee beverage, a black tea beverage, a green tea beverage, a juice, and the like). Further, foods and drinks can also be produced by adding the food and drink composition to the above various publicly known foods and drinks.

3. Examples of Other Aspects in Accordance with the Present Invention

1) An egg allergy prevention method to be carried out with respect to a human infant, including:

a first administration period (first administration step) in which to administer, to an infant, heated egg powder (obtained by causing a heated egg to be in a form of dry powder) in an amount of 40 mg to 60 mg (equivalent to approximately 0.15 g to approximately 0.25 g of hard-boiled whole egg) per day; and a second administration period (second administration step) which is a period after the first administration period and in which to administer, to the infant, the heated egg powder in an amount of 220 mg to 280 mg (equivalent to approximately 0.88 g to approximately 1.25 g of the hard-boiled whole egg) per day.

2) The egg allergy prevention method mentioned in 1), wherein in the first administration period, the heated egg powder is administered in an amount of 45 mg to 55 mg per day.

3) The egg allergy prevention method mentioned in 1) or 2), wherein in the first administration period, the heated egg powder is administered in an amount of 48 mg to 52 mg (more preferably of 49 mg to 51 mg) per day.

4) The egg allergy prevention method mentioned in any one of 1) through 3), wherein in the second administration period, the heated egg powder is administered in an amount of 240 mg to 260 mg per day.

5) The egg allergy prevention method mentioned in 4), wherein in the second administration period, the heated egg powder is administered in an amount of 245 mg to 255 mg (more preferably of 248 mg to 252 mg) per day.

6) The egg allergy prevention method mentioned in any one of 1) through 5), wherein the first administration period is 2 or more consecutive months (preferably not less than 2 and not more than 4 consecutive months, and more preferably not less than 2.5 and not more than 3.5 consecutive months) selected from a period from 4 months to less than 10 months of age (preferably a period from 6 months to less than 9 months of age) of the infant.

7) The egg allergy prevention method mentioned in any one of 1) through 6), wherein the second administration period is 2 or more consecutive months (preferably not less than 2 and not more than 4 consecutive months, and more preferably not less than 2.5 and not more than 3.5 consecutive months) selected from a period from 8 months to not more than 12 months of age (preferably a period from 9 months to not more than 12 months of age) of the infant.

8) The egg allergy prevention method mentioned in any one of 1) through 7), wherein the egg allergy prevention method is to be carried out with respect to the infant who has eczema or has a history of eczema (e.g., the infant who has atopic dermatitis or the infant who has developed eczema by 4 months of age or 5 months of age).

9) The egg allergy prevention method mentioned in 8), wherein the egg allergy prevention method is carried out concurrently with treatment of the eczema (e.g., atopic dermatitis).

10) The egg allergy prevention method mentioned in any one of 1) through 9), wherein the heated egg powder is orally administered to the infant.

11) The egg allergy prevention method mentioned in any one of 1) through 10), wherein the heated egg powder is administered to the infant on not less than 70% of days (preferably not less than 80% of the days, not less than 90% of the days, not less than 95% of the days, and 100% of the days (i.e., every day)) included in each of the first administration period and the second administration period.

11A) The egg allergy prevention method mentioned in any one of 1) through 11), further including:

a further administration period (further administration step) which is different from each of the first administration period (first administration step) and the second administration period (second administration step) and which is between the first administration period and the second administration period, in the further administration period (further administration step), the heated egg powder being administered to the infant in a greater amount per day than in an administration period followed by the further administration period (e.g., the first administration period), and in a smaller amount per day than in an administration period following the further administration period (e.g., the second administration period).

In the further administration period, the heated egg powder is administered to the infant in an amount of, for example, 80 mg to 120 mg or 90 mg to 110 mg.

11B) The egg allergy prevention method mentioned in any one of 1) through 11), and 11A), wherein preceding and following administration periods (For example, the preceding and following administration periods are the first administration period and the second administration period. In a case where the further administration period is present, the preceding and following administration periods are the first administration period, the further administration period, and the second administration period) are continuous with each other.

12) An egg allergy prevention pharmaceutical composition combination (a combination of pharmaceutical compositions for egg allergy prevention) to be administered to a human infant, containing:

an egg allergy prevention pharmaceutical composition (1) containing heated egg powder in an amount of 40 mg to 60 mg; and an egg allergy prevention pharmaceutical composition (2) containing heated egg powder in an amount of 220 mg to 280 mg.

13) The egg allergy prevention pharmaceutical composition combination mentioned in 12), wherein a period in which to administer the egg allergy prevention pharmaceutical composition (2) (a second administration period) begins after a period in which to administer the egg allergy prevention pharmaceutical composition (1) (a first administration period) ends.

14) An egg allergy prevention pharmaceutical composition (1) to be administered to a human infant, containing heated egg powder in an amount of 40 mg to 60 mg (equivalent to approximately 0.15 g to approximately 0.25 g of hard-boiled whole egg).

15) An egg allergy prevention pharmaceutical composition (2) to be administered to a human infant, containing heated egg powder in an amount of 220 mg to 280 mg (equivalent to approximately 0.88 g to approximately 1.25 g of hard-boiled whole egg).

16) The egg allergy prevention pharmaceutical composition or the egg allergy prevention pharmaceutical composition combination mentioned in any one of 12) through 15), wherein the egg allergy prevention pharmaceutical composition (1) contains the heated egg powder in an amount of 45 mg to 55 mg.

17) The egg allergy prevention pharmaceutical composition or the egg allergy prevention pharmaceutical composition combination mentioned in 16), wherein the egg allergy prevention pharmaceutical composition (1) contains the heated egg powder in an amount of 48 mg to 52 mg (more preferably of 49 mg to 51 mg).

18) The egg allergy prevention pharmaceutical composition or the egg allergy prevention pharmaceutical composition combination mentioned in any one of 12) through 17), wherein the egg allergy prevention pharmaceutical composition (2) contains the heated egg powder in an amount of 240 mg to 260 mg.

19) The egg allergy prevention pharmaceutical composition or the egg allergy prevention pharmaceutical composition combination mentioned in 18), wherein the egg allergy prevention pharmaceutical composition (2) contains the heated egg powder in an amount of 245 mg to 255 mg (more preferably of 248 mg to 252 mg).

20) The egg allergy prevention pharmaceutical composition or the egg allergy prevention pharmaceutical composition combination mentioned in any one of 12) through 19), wherein the egg allergy prevention pharmaceutical composition (1) is to be administered to the infant whose age is 4 months to 10 months (preferably 6 months to 9 months).

21) The egg allergy prevention pharmaceutical composition or the egg allergy prevention pharmaceutical composition combination mentioned in any one of 12) through 20), wherein the egg allergy prevention pharmaceutical composition (2) is to be administered to the infant whose age is 8 months to 12 months (preferably 9 months to 12 months).

22) The egg allergy prevention pharmaceutical composition or the egg allergy prevention pharmaceutical composition combination mentioned in any one of 12) through 21), wherein the egg allergy prevention pharmaceutical composition or the egg allergy prevention pharmaceutical composition combination is to be administered to the infant who has eczema or has a history of eczema (e.g., the infant who has atopic dermatitis or the infant who has developed eczema by 4 months of age or 5 months of age).

23) The egg allergy prevention pharmaceutical composition or the egg allergy prevention pharmaceutical composition combination mentioned in any one of 12) through 22), wherein the egg allergy prevention pharmaceutical composition or the egg allergy prevention pharmaceutical composition combination is for use in oral administration.

23A) The egg allergy prevention pharmaceutical composition or the egg allergy prevention pharmaceutical composition combination mentioned in any one of 12) through 23), further containing an egg allergy prevention pharmaceutical composition (3) containing heated egg powder in an amount of 80 mg to 120 mg or 90 mg to 110 mg.

23B) The egg allergy prevention pharmaceutical composition or the egg allergy prevention pharmaceutical composition combination mentioned in 23A), wherein:

a further administration period which is different from each of the first administration period and the second administration period is between the first administration period and the second administration period; and the egg allergy prevention pharmaceutical composition (3) is administered to the infant in the further administration period.

23C) The egg allergy prevention pharmaceutical composition or the egg allergy prevention pharmaceutical composition combination mentioned in 23A) or 23B), wherein preceding and following administration periods (For example, the preceding and following administration periods are the first administration period and the second administration period. In a case where the further administration period is present, the preceding and following administration periods are the first administration period, the further administration period, and the second administration period) are continuous with each other.

24) The egg allergy prevention pharmaceutical composition or the egg allergy prevention pharmaceutical composition combination mentioned in any one of 1) through 23), 23A), 23B), and 23C), wherein the heated is whole egg thereof.

The present invention is not limited to the embodiments, but can be altered by a skilled person in the art within the scope of the claims. The present invention also encompasses, in its technical scope, any embodiment derived by combining technical means disclosed in differing embodiments.

Example

The following will further specifically describe the present invention with reference to Examples, Comparative Examples, etc. below. However, the present invention is not limited to these.

Summary of Examples

Background Evidence is accumulating that early consumption is more beneficial than is delayed introduction as a strategy for primary prevention of food allergy. However, allergic reactions caused by early introduction of such solid foods have been a problematic issue. We investigated whether or not early stepwise introduction of eggs to infants with eczema combined with optimal eczema treatment would prevent egg allergy at 1 year of age.

Methods In this randomised, double-blind, placebo-controlled trial, we enrolled infants 4-5 months of age with eczema from two centres in Japan. Exclusion criteria were being born before 37 weeks of gestational age, experience of ingestion of hen's eggs or egg products, history of immediate allergic reaction to hen's eggs, history of non-immediate allergic reaction to a particular type of food, and complications of any severe disease. Infants were randomly assigned (block size of four; stratified by institution and sex) to early introduction of egg or placebo (1:1). Participants in the egg group consumed orally 50 mg of heated egg powder per day from 6 months to 9 months of age and 250 mg per day thereafter until 12 months of age. We aggressively treated participants' eczema at entry and maintained control without exacerbations throughout the intervention period. Participants and physicians were masked to assignment, and allocation was concealed. The primary outcome was the proportion of participants with hen's egg allergy confirmed by open oral food challenges at 12 months of age, assessed blindly by standardised methods, in all randomly allocated participants who received the intervention. This trial is registered with the University Hospital Medical Information Network Clinical Trials Registry, number UMIN000008673.

Findings Between Sep. 18, 2012, and Feb. 13, 2015, we randomly allocated 147 participants (73 [50%] to the egg group and 74 [50%] to the placebo group). This trial was terminated on the basis of the results of the scheduled interim analysis of 100 participants, which showed a significant difference between the two groups (four [9%] of 47 participants had an egg allergy in the egg group vs 18 [38%] of 47 in the placebo group; risk ratio 0.222 [95% CI 0.081-0.607]; p=0.0012). In the primary analysis population, five (8%) of 60 participants had an egg allergy in the egg group compared with 23 (38%) of 61 in the placebo group (risk ratio 0.221 [0.090-0.543]; p=0.0001). The only difference in adverse events between groups was admissions to hospital (six [10%] of 60 in the egg group vs none in the placebo group; p=0.022). 19 acute events occurred in nine (15%) participants in the egg group versus 14 events in 11 (18%) participants in the placebo group after intake of the trial powder.

Interpretation Introduction of heated egg in a stepwise manner along with aggressive eczema treatment is a safe and efficacious way to prevent hen's egg allergy in high-risk infants. In this study, we developed a practical approach to overcome the second wave of the allergic epidemic caused by food allergy. This method is also a safe and efficacious way to prevent hen's egg allergy in infants without eczema.

Research in Context

Evidence Before this Study

We searched PubMed and Embase between Jan. 29, 2016, and Mar. 31, 2016, in the English language, using the following search terms; "infant", "eczema", "prevention", "allergy", and "randomised controlled trial". The Food Allergy and Anaphylaxis Guidelines published by the European Academy of Allergy and Clinical Immunology reported that "the present evidence does not justify recommendations about either withholding or encouraging exposure to potentially allergenic foods after the age of 4 months". The Consensus Communication on Early Peanut Introduction and the Prevention of Peanut Allergy in High-Risk Infants was released in 2015 on the basis of the Learning Early About Peanut Allergy trial data, which provided Level 1 evidence that early introduction of peanuts is safe and effective in selected high-risk infants at reduction of subsequent peanut allergy by up to 81%. The Enquiring About Tolerance study was a randomised controlled trial that recruited infants from the general population, assessing whether or not early exposure might reduce subsequent allergy. The per-protocol analysis suggested a possible protective effect of early introduction of peanuts and hen's eggs, but adherence to the study protocol was rather low and the results in the intention-to-treat analysis were negative. In addition to the Learning Early About Peanut Allergy and Enquiring About Tolerance studies, we identified only one trial published in 2013 describing the preventive effect of early introduction of eggs for high-risk infants with eczema. Investigators reported that a lower proportion of infants in the early egg introduction group 12 months of age than in the placebo group (18 [51%] of 35); however, the difference did not reach statistical significance (relative risk 0.65 [95% CI 0.38-1.11]). Caution is needed when infants with moderate-to-severe eczema are first exposed to eggs because many have already developed sensitisation and clinical reactivity by 4 months of age.

Added Value of this Study

This trial is the first randomised, double-blind, placebo-controlled trial to produce results that show a safe and effective method of early introduction of hen's eggs to high-risk infants with eczema to prevent egg allergy. Our findings substantiate that early introduction of a small amount of heated egg in a stepwise manner combined with attentive treatment of eczema can reduce the prevalence of egg allergy in high-risk infants with eczema.

Implications of all the Available Evidence

Our results provide firm evidence that early introduction of potentially allergenic foods can be done safely by starting from a small dose and that prevention of food allergy can be achieved effectively in a stepwise manner. A small amount of solid food is safe, even for sensitised infants, and this stepwise approach is practical at a population level because infants do not need to be screened by skin prick, serum-specific IgE concentration, or challenge tests before introduction. Additional trials are needed to test this approach for prevention of other types of food allergies. Optimal control of eczema might be an integral part of the preventive programme to minimise the chance of percutaneous sensitisations.

Methods

Study Design and Participants

In this randomised, double-blind, placebo-controlled trial, we recruited patients from the National Center for Child Health and Development (NCCHD) and Tachikawa Sougo General Hospital (TSGH) in Tokyo, Japan. Participants were eligible for enrolment if they were 4-5 months of age with atopic dermatitis meeting Hanifin-Rajkas' diagnostic criteria [Non-Patent Literature 18]. Exclusion criteria were being born before 37 weeks of gestational age, experience of ingestion of hen's eggs or egg products, history of immediate allergic reaction to hen's eggs, history of non-immediate allergic reaction to a particular type of food, and complications of any severe disease. We did not exclude any individual for introduction of any solid food except for egg. We obtained written informed consent from the parents of the participants at the time of enrolment. The study was approved by the institutional review board of the NCCHD and TSGH. The protocol for this study and the subsequent changes are available at the NCCHD website.

Randomisation and Masking

Participants were randomly assigned to the egg or placebo group in a ratio of 1:1. Allocation was carried out with use of the block randomisation method. The block size was four, and participants were stratified into four groups based on institution (TSGTH or NCCHD) and sex. The allocation plan was created by the Data Centre located at the NCCHD. The Data Centre was in charge of randomisation of participants and storage of all clinical data. The following procedure was adopted to conceal allocation information: at the time of registration of a participant, the Data Centre received information about institution and sex only, and they allocated an assignment code a or b, without knowing the identity of the participant. Assignment was executed on the basis of a computer-generated random number table. The result of the assignment was orally communicated to a designated member of clinical staff, who was the only person to know which assignment code corresponded to the egg or placebo group. This staff member prepared the trial powder for distribution to participants without being involved in any other aspect of the study. Participants were recruited by those giving the intervention (ON, SK, JN, KY-H, MK, MS, and AK) and PETIT study members (listed in the appendix (FIGS. 5-17)) and the primary and secondary outcomes were assessed by the other masked outcome assessors (PETIT study members). In this way, participants, their caregivers, those giving the intervention, outcome assessors, and the Data Centre were all masked to assignment information during the trial, and allocation was concealed. Only the Independent Data and Safety Monitoring Committee (IDSMC) could access the unmasked data.

Procedures

Participants consumed orally the allocated trial powder from 6 months of age daily, for 6 months. We assigned the egg group a powder consisting of egg and squash (Japanese pumpkin), whereas we assigned the placebo group a powder consisting of squash, for which we matched colour and volume with the egg powder (appendix (FIGS. 5-17)). For the egg group, we prepared packages containing two different doses of egg powder. One taken daily for 3 months beginning from 6 months of age consisted of 50 mg of heated egg powder (containing 25 mg of egg protein, which is equivalent to 0.2 g of whole egg boiled for 15 min) and 100 mg of squash. The other egg powder packages consumed for the last 3 months beginning from 9 months of age consisted of 250 mg heated egg powder (containing 125 mg egg protein, which is equivalent to 1.1 g of boiled whole egg) and squash. Our clinical experience of oral immunotherapy for egg allergy suggested that 50 mg of heated egg powder was a safe dose for first introduction. We adopted the two-step approach to increase the dose of egg powder 3 months after the first egg introduction. Correspondingly, we also provided the placebo group two different doses of trial powder packages containing squash, 150 mg from 6 months of age and 250 mg from 9 months of age (appendix (FIGS. 5-17)).

On the first day of trial powder introduction at 6 months of age and the first dose-up day at 9 months of age, participants visited the hospitals to receive an oral food challenge test by using the assigned powder so that they could be carefully observed for 2 h after intake of the powder by a paediatric allergist. Subsequently, participants' consumption of the trial powder was recorded daily by their respective caregivers. We did not place participants under any food restrictions except for eggs and egg products. We did not require their mothers to follow any dietary restrictions, whether they were breastfeeding or not.

We treated participants' eczema attentively, aiming to achieve remission, and gave proactive therapy to some patients with moderate-to-severe eczema to prevent flare-up, as previously described [Non patent literature 19]. We treated participants for their eczema when they visited the hospitals as outpatients for the first time before enrolment in this study. Specifically, for infants with moderate-to-severe eczema, we applied topical corticosteroids (0.1% hydrocortisone butyrate ointment for the face and 0.12% betamethasone valerate ointment for everywhere else) daily until the eczema disappeared. Topical steroids would then be used intermittently for a maximum of 2 days a week for maintenance of remission. If remission was maintained for more than a month, we replaced application of steroid ointment with emollients and gradually tapered them off (appendix (FIGS. 5-17)). Participants had regular visits to outpatient units for assessment in addition to their scheduled visits for this trial to make sure that their eczema was in remission. We obtained blood samples at patients' first visits as outpatients, at enrolment (4-5 months of age), and at 9 months and 12 months of age. We did clinical assessments at the same timepoints. Adverse events were recorded in an event diary by caregivers and physicians checked the diary at every scheduled or unscheduled visit.

The oral food challenge (OFC) consisted of a cumulative dose of 7 g of heated whole-egg powder equivalent to 32 g of boiled whole hen's eggs in both groups. If a participant showed any objective immediate allergic reactions, such as urticaria, continuous cough, wheezing, vomiting, or diarrhoea, the participant would be diagnosed as having hen's egg allergy. Additional information about OFC is provided in the appendix (FIGS. 5-17). We measured serum concentrations of IgE specific to egg white and ovomucoid with the ImmunoCAP (Thermo Fisher Scientific, Upsala, Sweden) system. We measured serum concentrations of IgG1, IgG4, and IgA specific to egg white and ovomucoid with a microarray system using diamond-like carbon-coated densely carboxylated protein chips [Non patent literature 20].

We collated baseline data at enrolment (4-5 months old), but measured Scoring Atopic Dermatitis (SCORAD) [Non patent literature 21] and thymus and activation-regulated chemokine (TARC) data at the time of patients' first visits as outpatients, even if this visit was before 4 months of age, to record patients' initial skin conditions before they started eczema treatment. We recorded each participant's skin condition using SCORAD and the patient-oriented eczema measure (POEM) [Non patent literature 22]. We assessed SCORAD at the first visit as baseline data and again at 12 months of age. POEM was assessed by a caregiver weekly during the trial. We used mean POEM score for 4 weeks as the score for each month.

Outcomes

The primary outcome was the proportion of participants with hen's egg allergy confirmed by open OFC at 12 months of age. Secondary outcomes were serum egg white and ovomucoid-specific IgE, IgG4, and IgA concentrations, together with TARC concentration. Although we planned to measure salivary antigen-specific immunoglobulin concentration as a secondary outcome, we were unable to measure it because of technical reasons. We measured egg-specific immunoglobulin concentration at enrolment (4-5 months of age) as baseline data and at 9 months and 12 months of age. We measured TARC concentration at participants' first visit as outpatients before enrolment (as baseline data) and then at 9 months and 12 months of age (appendix (FIGS. 5-17)). The safety outcome was the proportion of infants with serious adverse events and important medical events during taking of trial powders. Changes of outcomes after the trial was started are described in the protocol.

Statistical Analysis

We predicted the prevalence of IgE-mediated egg allergy at 12 months of age to be 7% in the egg consumption group and 20% in the placebo group on the basis of published reports [Non patent literatures 8, 23]. To detect a relative reduction of 65% (from 20% to 7%), with a power of 80% ($\alpha$=0.05 [two-sided]), we estimated that 92 infants per group were needed. Allowing for about 10% loss to follow-up, we planned to recruit 200 infants.

We analysed the primary outcome in all randomly allocated participants who received the intervention. We excluded participants whose parents voluntarily withdrew them from the analysis before they started the intervention and considered those who were withdrawn after they started the intervention positive for the primary outcome. We included participants who satisfied the recruitment criteria, took a trial powder for more than 130 days, and accidentally ingested hen's egg outside of the trial less than twice in the per-protocol analysis. We excluded participants whose primary outcome was not established when the trial ceased (on the basis of the results of the interim analysis) from the primary analysis population, the per-protocol analysis, and baseline data. We analysed adverse events in the primary analysis population.

Interim analysis by the IDSMC was scheduled for 1 year after the start of the study or when the number of participants reached 100. At interim analysis, we planned a point estimate for the primary outcome and if the estimated intervention effect was different from the value used in the sample size calculation, we would recalculate the required sample size. Decision making about changing of the total number recruited on the basis of the interim analysis would be done by the IDSMC, not by the trial steering committee, which was masked to assignment.

We analysed the primary outcome with the $x^2$ test. We set the level of statistical significance for the primary outcome at 0.05 (two-sided). We also did post-hoc logistic regression analysis to take into account stratification factors and imbalances of baseline variables between groups, including SCORAD score, family history of allergic diseases, and start of solid foods. We also did subgroup analyses stratified by concentration of egg white-specific IgE at baseline (we defined lower than 0.35 kUA/L as non-sensitised) in the primary analysis and per-protocol analysis populations. Furthermore, we did analyses stratified by the class of egg white and ovomucoid-specific IgE at baseline in the per-protocol analysis population. We also did logistic regression analysis, adjusting for the following covariates: serum TARO, total IgE, and egg white-specific IgE concentrations at baseline and mean POEM score from 6-12 months of age. We did safety analyses in the primary analysis population using $x^2$ and Wilcoxon rank-sum tests. We did all statistical analyses using R version 3.1.0. This trial was overseen by the IDSMC. This trial is registered with the University Hospital Medical Information Network Clinical Trials Registry, number UMIN000008673).

Supplement to the Methods

Procedures

Intervention

During the two-week period before and after six months of age, participants assigned to the egg group started daily ingestion of an egg trial powder consisting of 50 mg heated whole egg powder (Kewpie Corporation, JAPAN), which is equivalent to 0.2 g of whole egg boiled for 15 minutes, mixed with 100 mg of squash powder (Kabotcha powder®, Mikasa Sangyo Co, JAPAN) and 150 mg of glucose. Starting at the same age, participants in the placebo group started daily ingestion of a trial powder consisting of 150 mg of squash powder mixed with 150 mg of glucose.

During the two-week period before and after nine months of age, the quantity of the egg-containing trial powder was increased to 250 mg of heated whole egg powder (equivalent to 1.1 g of whole boiled egg) mixed with 250 mg of glucose, while the placebo powder was increased to 250 mg of squash powder mixed with 250 mg glucose. Participants in both groups were instructed to keep taking the trial powders once a day until they underwent the OFC.

Outcome

Oral Food Challenge

The primary outcome was the incidence of hen's egg allergy proven by provocation test at 12 months of age. In the open oral food challenge, participants in both groups ingested heated whole egg powder divided with 3 doses every 30 minutes. The amount of the egg powder ingested was 1 g for the first time, 2 g for the second time and 4 g for the third time. The cumulative dose of powder was equivalent to 32 g of whole hen's egg boiled for 15 minutes. If a participant showed any objective immediate allergic reactions, such as urticaria, continuous cough, wheezing, vomiting and/or diarrhea, he/she was diagnosed as having hen's egg allergy.

Results

Figure 1:
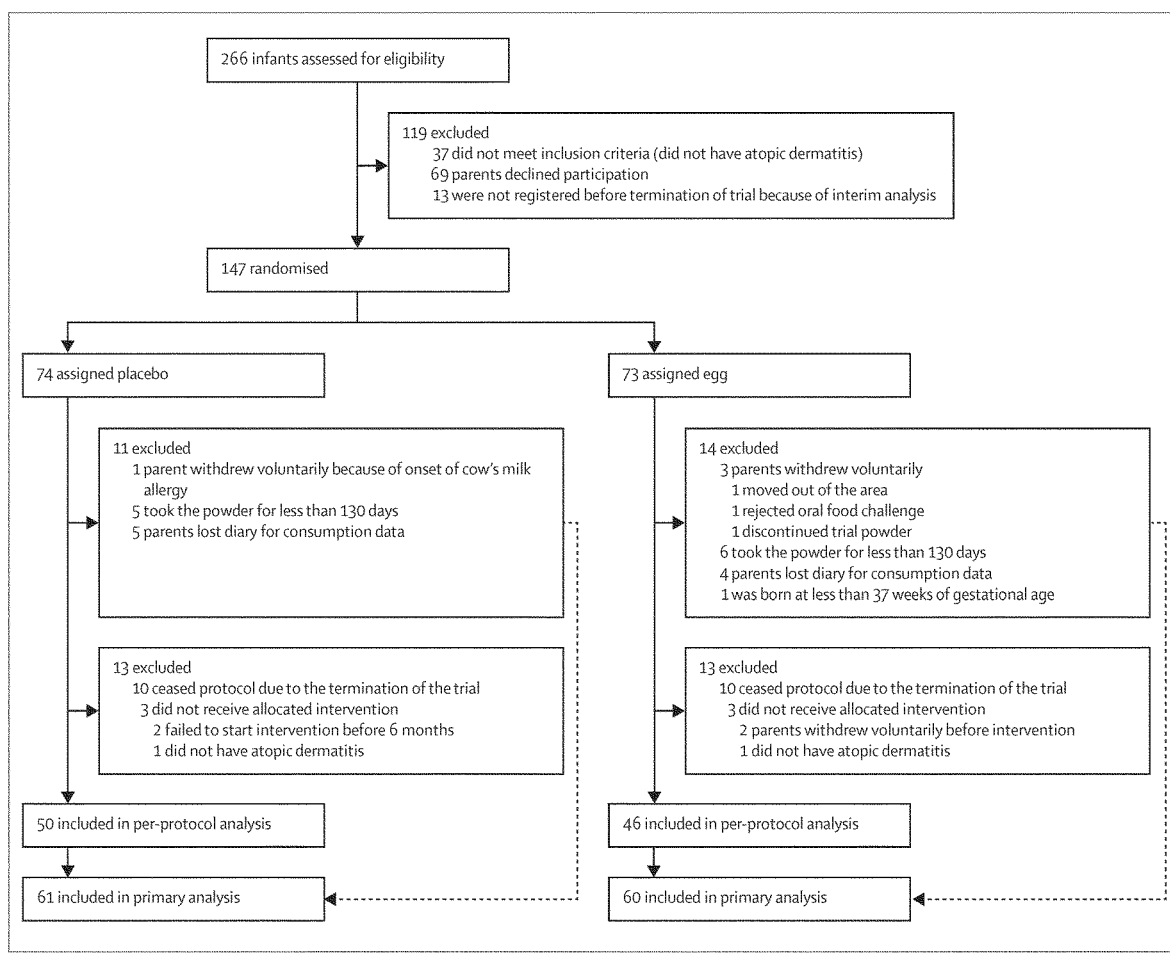
FIG. 1 relates to the trial profile.

Between Sep. 18, 2012, and Feb. 13, 2015, we assessed 266 infants for their eligibility, successfully enrolling 147 (55%) of them on the basis of the inclusion and exclusion criteria (FIG. 1). We allocated 73 participants (50%) to the egg group and 74 (50%) to the placebo group. We stopped recruitment early at the request of the IDSMC because the interim analysis of the first 100 participants detected a significant difference between the two groups in the primary outcome. Six (6%) participants were excluded from this analysis (and the final analysis) because they never consumed a trial powder (three [6%] in each group): two (2%) were found to not meet the diagnostic criteria for atopic dermatitis (one [2%] in each group) and four (4%) did not start the intervention (two [4%] in each group), Allocation was opened to all investigators and participants after fixing of the data, on May 15, 2015.

The number of participants included in the primary analysis was 60 (50%) in the egg group and 61 (50%) in the placebo group. We excluded 20 (14%) participants from the final analysis who had not been assessed by the provocation test when the trial ceased and were asked to stop their participation (ten [14%] in each group). 117 (97%) of 121 participants were assessed for the primary outcome by OFC (70 [96%] of 73 in the egg group and 73 [99%] of 74 in the placebo group). One (1%) participant in the placebo group and three (4%) in the egg group withdrew from the trial (appendix (FIGS. 5-17)); they were included in the primary analysis but excluded from the per-protocol analysis. With regard to adherence, six (8%) participants in the egg group and five (7%) in the placebo group were excluded from per-protocol analysis because they had taken the trial powder for less than 130 days. In the per-protocol analysis population, the mean number of consumption days of the trial powder was 163.5 days (SD 17.9) in the egg group and 167.6 days (16.5) in the placebo group. Baseline characteristics are shown in table 1 and the appendix (FIGS. 5-17). More than 90% of participants received breastfeeding at 6 months of age.

The number of patients with hen's egg allergy confirmed by OFC at 12 months of age was four (9%) of 47 in the egg group and 18 (38%) of 47 in the placebo group at interim analysis. The IDSMC requested the person in charge of statistics in this trial (EI) to calculate the significance of difference, although this calculation was not planned at the interim analysis in the statistical analysis plan. The risk ratio was 0.222 (95% CI 0.081-0.607; p=0.0012), which crossed O'Brien-Fleming's boundary; the corresponding significance level was 0.003.

Figure 2:
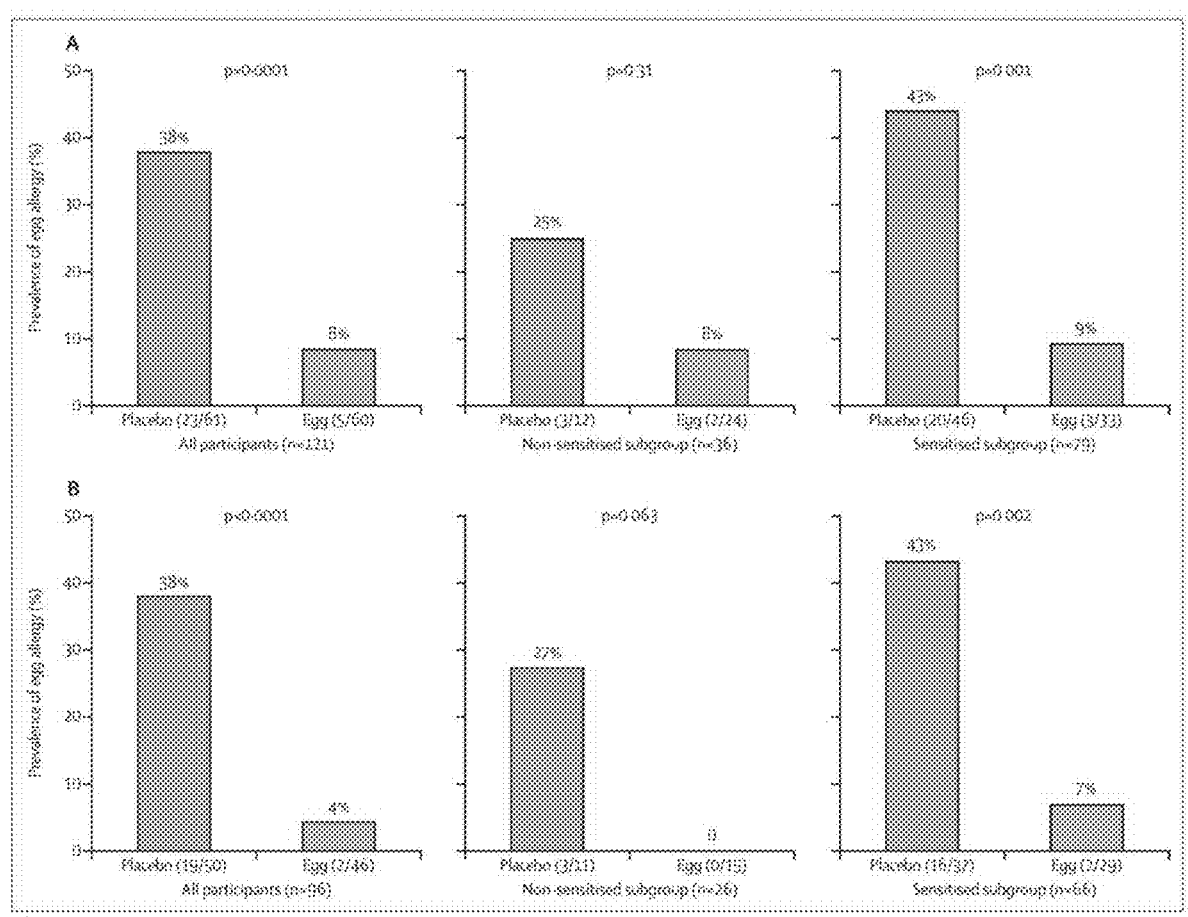
FIG. 2 relates to prevalence of egg allergy. (A) Primary analysis population. (B) Per-protocol analysis. The left panels show all participants. The middle and right panels show the subgroup analysis that stratified by concentration of egg white-specific IgE at baseline into lower (non-sensitised subgroup; middle panels) or higher (sensitised subgroup; right panels) than 0.35 kuA/L. We used $x^2$ tests for all participants and Fisher's exact tests for subgroup analyses.

In the primary analysis population, five (8%) of 60 in the egg group and 23 (38%) of 61 in the placebo group had hen's egg allergy confirmed by OFC at 12 months of age. The risk difference was 29.4% (95% CI 15.3-43.4), the number needed to treat was 3.40 (2.30-6.52), and the risk ratio was 0.221 (0.090-0.543; p=0.0001; FIG. 2). The odds ratio of the two groups was 0.113 (95% CI 0.035-0.361) adjusted for SCORAD score, 0.161 (0.056-0.468) adjusted for allergic history of father and mother, and 0.083 (0.023-0-297) adjusted for start of solid foods (appendix (FIGS. 5-17)). For worst scenario analysis in which withdrawers from the egg group are considered positive for the primary outcome and those from the placebo group as negative, five (8%) of 60 participants in the egg group had confirmed egg allergy compared with 22 (36%) of 61 in the placebo group (p=0.0002). In the per-protocol analysis, two (4%) of 46 participants in the egg group were diagnosed as having hen's egg allergy compared with 19 (38%) of 50 participants in the placebo group (FIG. 2). The risk difference was 33.7% (95% CI 19.0-48.3) and the risk ratio was 0.114 (0.028-0.464; p<0.0001). The number needed to treat was 2.97 (2.07-5.27) and the relative reduction in the prevalence of hen's egg allergy in the egg group compared with the placebo group was 89%.

Figure 3:
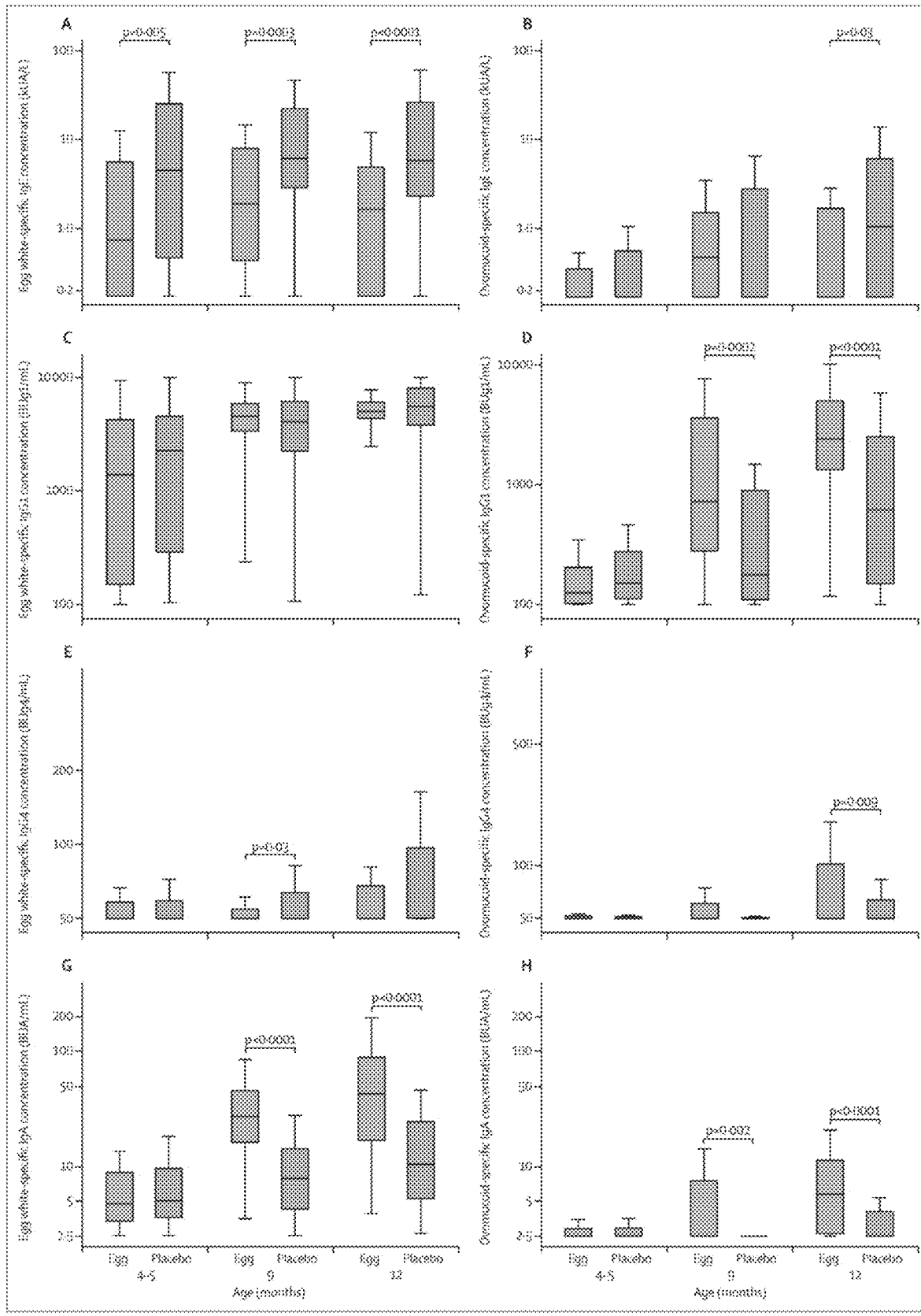
FIG. 3 relates to immunoglobulin concentration. Changes in (A) egg white-specific IgE, (B) ovomucoid-specific IgE, (C) egg white-specific IgG1, (D) ovomucoid-specific IgG1, (E) egg white-specific IgG4, (F) ovomucoid-specific IgG4, (G) egg white-specific IgA, and (H) ovomucoid-specific IgA concentrations. We used Wilcoxon rank-sum tests to compare immunoglobulin concentrations between the placebo and egg groups. *$p<0.5$.
Figure 4:
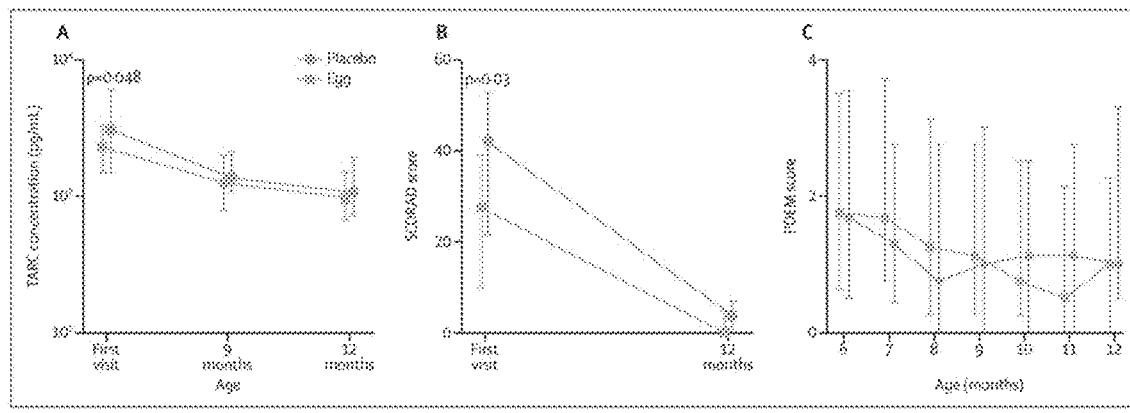
FIG. 4 relates to markers of participants' skin conditions. Change in (A) serum thymus and activation-regulated chemokine concentration, (B) Scoring Atopic Dermatitis score, and (C) patient-oriented eczema measure (POEM) score. We measured serum thymus and activation-regulated chemokine concentration and Scoring Atopic Dermatitis score at the first visit as outpatients. We recorded POEM score during treatment (6-12 months of age). We treated the mean POEM score during 4 weeks as the score for each month. We used Wilcoxon rank-sum tests. Error bars are IQRs. POEM=patient-oriented eczema measure. Error bars are IQRs. SCORAD=Scoring Atopic Dermatitis. TARC=thymus and activation-regulated chemokine. *$p<0.05$ FIG. 5 relates to the trial design. Participants were enrolled between four and five months of age. Participants in both groups took the trial powder daily from six to 12 months of age, with an increase in the amount of the trial powder onwards from nine months of age. At 12 months of age, participants in both groups underwent oral food challenge with a total of 7 g of heated whole egg powder.
Figure 5:
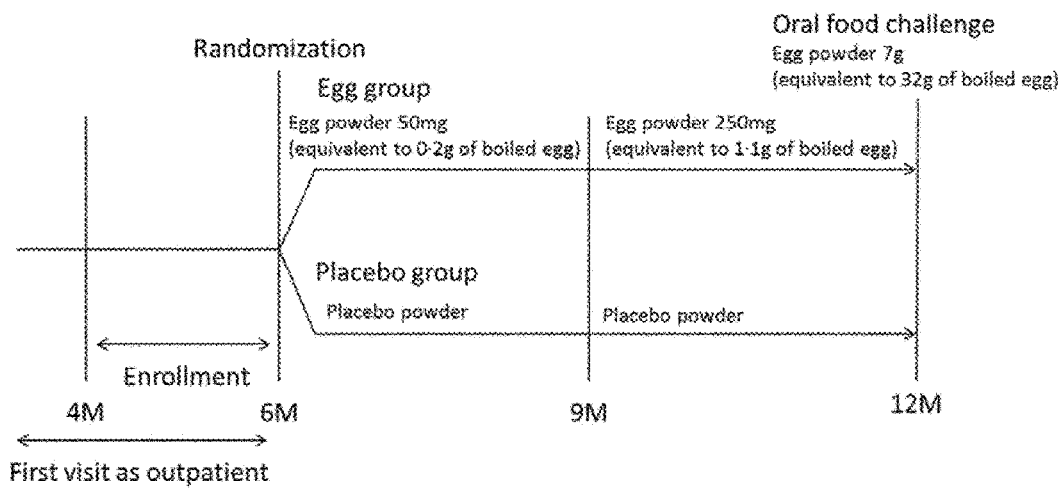
Figure 6:
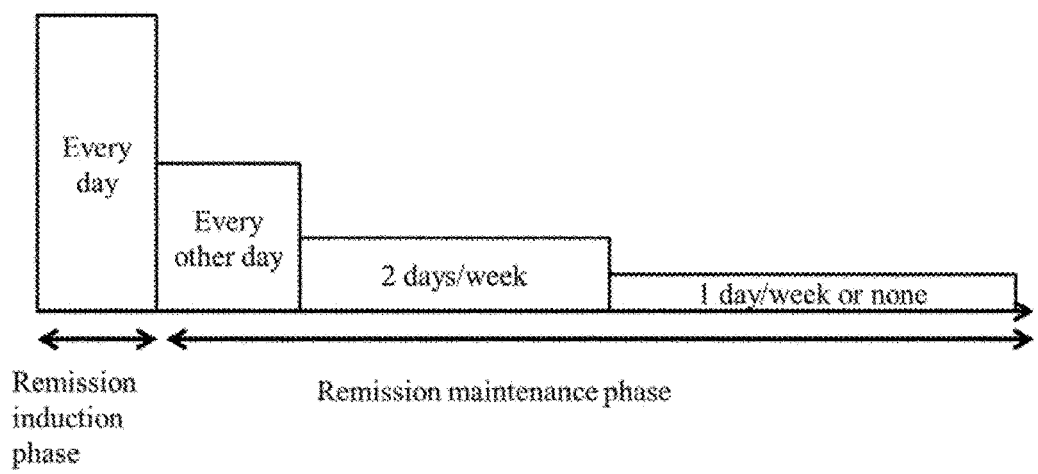
FIG. 6 relates to the Application of corticosteroid ointment for eczema.

Ovomucoid-specific IgE concentration at 12 months of age in the egg group was lower than that in the placebo group, whereas ovomucoid-specific IgG1, IgG4, and IgA concentrations at 12 months of age were higher in the e g group than in the placebo group (FIG. 3, appendix (FIGS. 5-17)). Sequential changes of egg white-specific and ovomucoid-specific IgE concentrations of individual participants are shown in the appendix (FIGS. 5-17). Egg white-specific IgE and ovomucoid-specific IgE and IgG4 concentrations of participants with egg allergies in the placebo group were increased compared with those without egg allergies (appendix (FIGS. 5-17)). TARC concentration at 9 months and 12 months of age and SCORAD score at 12 months of age were decreased from baseline in both groups (FIG. 4). POEM scores during the intervention were low in both groups, suggesting that the eczema was well maintained during the trial in both groups. The two (3%) participants who developed egg allergy in the egg group in the per-protocol analysis had a higher POEM score than did the other participants (appendix (FIGS. 5-17)).

The only difference between groups in adverse events was the total number of admissions to hospital (table 2). Five (8%) participants in the egg group were admitted to hospital (a total of six times) during the intervention. The number of participants diagnosed as being affected with asthma according to the Japanese guideline's criteria4 was not significantly different between groups. Four (3%) participants (three [5%] in the egg group and one [2%] in the placebo group; details shown in the appendix (FIGS. 5-17)) withdrew from the trial after commencement of the intervention. No participants withdrew because of adverse reactions caused by the trial powder (appendix (FIGS. 5-17)). No acute sign occurred when participants ingested the trial powder for the first time at the outpatient unit of the hospital at 6 months and 9 months of age. Although a few participants had urticaria 4 h or longer after ingestion of trial powder, skin rash around the mouth, angioedema of the lip, vomiting, transient worsening of eczema, bloody stool, or diarrhoea lasting 10 days or longer after intake of the trial powder at home, we noted no difference in reported numbers between the two groups (19 events in nine [15%] infants in the egg group versus 14 events in 11 [18%] infants in the placebo group). Furthermore, infants who showed acute signs of angioedema of the lip or vomiting were able to continue taking the trial egg powder without developing the same symptom again. Other adverse events were also not different between groups.

We carried out post-hoc analyses to explore the effects of stratification factors and baseline imbalances between the two groups. For the subgroup analysis by stratification with use of the concentration (0.35 kUa/L) of egg white-specific IgE at baseline, in the non-sensitised subgroup, two (8%) of 24 participants in the egg group and three (25%) of 12 in the placebo group were diagnosed as being affected with hen's egg allergy (risk difference 16.7% [95% CI-10.2 to 43.5]; p=0.31; FIG. 2). In the sensitised subgroup, three (9%) of participants in the egg group and 20 (43%) of 46 participants in the placebo group were diagnosed as being affected with hen's egg allergy (risk difference 34.4% [17.0-51.7]; p=0.001). The subgroup analysis in the per-protocol analysis population showed similar results to those of the subgroup analysis in the primary analysis population (FIG. 2). We also analysed the primary outcome in the per-protocol analysis population with stratification by the class of egg white and ovomucoid-specific IgE concentration at baseline (appendix (FIGS. 5-17)). Comparing both groups in the participants of the same IgE class, the positive ratio of OFC in the placebo group tended to be higher than that in the egg group at 12 months of age.

The odds ratio of positive OFC by logistic regression analysis was 0.149 (95% CI 0.052-0.428) adjusted for sex, 0.156 (0.054-0.451) adjusted for TARC concentration, 0.206 (0.068-0.622) adjusted for total IgE concentration, 0.189 (0.063-0.565) adjusted for egg white-specific IgE concentration at baseline, and 0.063 (0.014-0.287) adjusted for mean POEM score from 6 months to 12 months of age in the primary analysis population, and findings were similar in the per-protocol analysis population (appendix (FIGS. 5-17)).

Discussion

In this trial, we found that hen's egg could be introduced to high-risk infants with atopic dermatitis with use of a two-step approach without immediate allergic reaction, even for participants who had IgE sensitisation to hen's egg before starting the intervention. In a previous RCT [Non patent literature 13], a high proportion (31%) of infants had allergic reactions to pasteurised raw egg powder. In our trial, no participants had an allergic reaction to the heated egg powder. Such a difference might be due to the higher allergenicity of raw than heated egg powder. Use of a lower starting dose than in that trial might also contribute to the safety of our approach. In the LEAP study [Non patent literature 12], six (13%) of 47 infants who were skin prick test positive reacted to baseline peanut challenge. Infants who were already sensitised to egg before introduction might have developed an allergic reaction if they were given a high dose of heated or raw egg powder at the start. These findings suggest that our two-step approach starting from low dose introduction might be a safer method than that used in the LEAP study, which more naturally mirrors real life rather than screening high-risk infants with skin prick test or serum food-specific IgE concentration or a challenge test before introduction.

In our analyses for safety, we noted a difference in the total number of admissions to hospital between groups, but the incidence of urinary tract infection and Kawasaki disease was within the general prevalence found in Japanese children [Non patent literatures 25, 26]. Admissions to hospital for moderate wheezing attack is common in Japan and the incidence was within the normal range found in Japan [Non patent literature 24]. The incidence of asthma diagnosed with Japanese guideline's criteria [Non patent literature 24] at 12 months of age was not different between groups and wheezing attacks did not occur within 4 h of ingestion of egg powders. For the other safety measures, we noted no significant difference between groups. No participant withdrew from this trial because of adverse events, substantiating the safety of our approach.

Another important feature of this study was the assessment and treatment of atopic dermatitis prospectively. All participants received optimal eczema treatment throughout the trial, resulting in very low POEM scores [Non patent literature 22]. The prevalence of egg allergy in this trial was lower than that in a previous study [Non patent literature 13] (33% in the egg group and 51% in the placebo group). In our study, the two participants who developed egg allergy in the egg group in the per-protocol analysis had a higher POEM score than did the other participants. The risk of percutaneous sensitisation to egg might be higher in infants with uncontrolled eczema than in those with controlled eczema [Non patent literature 27]. However, further RCTs will be needed to test the role of optimal eczema treatment in prevention of subsequent development of food allergy.

Our study was terminated early because of an unexpectedly large group difference at the planned interim analysis, and caution is needed when the results are interpreted. First, the estimated group difference is possibly biased, resulting in a bigger difference between the two groups than if the trial was not terminated early. Second, the two groups had differences in some baseline characteristics, despite our strict masking and randomisation procedures. These differences might be attributed to the incidental difference in severity of eczema, which have affected the concentration of serum IgE and TARC [Non patent literatures 27, 28]. We examined whether or not the differences at baseline might have affected our results. Reassuringly, the results of the adjusted and subgroup analyses were consistent with those of the unadjusted analysis, except that the subgroup analysis in the non-sensitised subgroup was not significantly different between groups. The imbalance of baseline variables between groups has the potential to affect the results, but our post-hoc analyses revealed that the effect of such imbalance was small. The strength of our study was the excellent adherence, implying the practicability of our approach. The adherence rate in the Enquiring About Tolerance study [Non patent literature 14] was only 43%, suggesting that development of high-adherence approaches like ours is needed to improve the efficacy of early introduction of high-risk foods such as eggs and peanuts.

Our trial is the first to show that stepwise introduction of eggs combined with attentive eczema treatment reduces the prevalence of egg allergy in high-risk infants. Our approach also shows the practicality and effectiveness of this approach. Further studies are needed to establish if this stepwise approach might be effective in prevention of other food allergies and in the general population.

TABLES

TABLE 1

| Baseline characteristics | | |
|---|---|---|
|  | Placebo (n = 61) | Egg (n = 60) |
| Age at enrolment (days) | 163·4 (19·9) | 162·2 (21·5) |
| Male sex | 40 (66%) | 39 (65%) |
| Gestational age (weeks) | 39·1 (1·28) | 38·9 (1·18) |
| Birthweight (g) | 3108 (325·4) | 3163 (373·8) |
| Caesarean section | 6/53 (11%) | 8/57 (14%) |
| Age at onset of eczema (months) | 1·8 (1·1) | 2·0 (1·1) |
| SCORAD score | 42·0 (22·1-52·3) | 27·5 (10·3-38·2) |
| TARC (pg/mL) | 3165 (1532-5867) | 2297 (1525-3250) |
| Total IgE concentration (IU/mL) | 4·2 (15·9-181·0) | 16·5 (5·3-51·2) |
| Egg white-specific IgE concentration (kUA/L) | 4·46 (0·47-24·8) | 0·73 (0·17-5·55) |
| Ovomucoid-specific IgE concentration (kUA/L) | 0·35 (0·17-0·56) | 0·17 (0·17-0·35) |
| Paternal history of allergic disease | 34/60 (57%) | 40/57 (70%) |
| Maternal history of allergic disease | 37/60 (62%) | 38/57 (67%) |
| Have pets | 15/59 (25%) | 6/53 (11%) |
| Smoking in the household | 12/58 (21%) | 14/56 (25%) |
| Age at start of solid foods (months) | 5·6 (0·7) | 5·6 (0·7) |
| Hen's egg elimination by mother during lactation | 15/57 (26%) | 15/59 (25%) |
| Breastfeeding | | |
| at 6 months of age | 56/60 (93%) | 57/60 (95%) |
| at 12 months of age | 43/59 (73%) | 37/57 (65%) |
| POEM at 6 months of age | 2·9 (3·2) | 2·1 (2·8) |

Data are mean (SD), n (%), median (IQR), or n/N (%).
SCORAD = Scoring Atopic Dermatitis.
TARC = thymus and activation-regulated chemokine.
POEM = patient-oriented eczema measure.

TABLE 2

| Adverse events" | | | |
|---|---|---|---|
|  | Placebo (n = 61) | Egg (n = 60) | p value |
| All-cause admission to hospital | | | |
| Total number of admissions to hospital | 0 | 5 (8%); 6 | 0·02 |
| Moderate wheezing attack | 0 | 2 (3%); 3 | 0.16 |
| Urinary tract infection | 0 | 2 (3%); 2 | 0.16 |
| Kawasaki disease | 0 | 1 (2%); 1 | 0.32 |
| Immune system disorders at 12 months of age | | | |
| Asthma* | 2 (3%); 3 | 3 (5%); 12 | 0.68 |
| Food allergy other than hen's egg allergy† | 13 (21%); 13 | 9 (15%); 9 | 0.48 |
| Cow's milk allergy† | 7 (11%); 7 | 6 (10%); 6 | 1 |
| Wheat allergy† | 3 (5%); 3 | 1 (2%) 1 | 0.62 |
| Other food allergy† | 6 (10%), 6 | 3 (5%); 3 | 0.49 |
| Acute signs after intake of the trial powder at home during the trial | | | |
| Urticaria within 4 h after ingestion of trial powder | 0 | 0 | 1 |
| Urticaria 4 h or longer after ingestion of trial powder | 5 (3%); 7 | 2 (3%); 7 | 0.27 |
| Rash around the mouth | 2 (3%); 3 | 0 | 0.16 |
| Respiratory symptom | 0 | 0 | 1 |
| Angioedema of the lip | 0 | 1 (2%); 2 | 0.32 |
| Vomiting | 1 (2%), 1 | 1 (2%), 4 | 0.98 |
| Transient worsening of eczema | 0 | 3 (5%); 3 | 0.08 |
| Bloody stool | 1 (2%); 1 | 0 | 0.32 |
| Diarrhoea lasting 10 days longer | 2 (3%); 2 | 3 (5%); 3 | 0.64 |
| Infections until 12 months of age | | | |
| Acute gastroenteritis | 20 (33%); 28 | 15 (25%); 23 | 0.41 |
| Fever | 14 (23%); 27 | 17 (28%); 35 | 0.51 |
| Upper respiratory infection | 30 (49%); 44 | 31 (52%); 51 | 0.60 |
| RS virus infection | 0 | 2 (3%), 2 | 0.16 |
| Influenza virus infection | 1 (2%), 1 | 1 (2%); 1 | 0.99 |
| Adenovirus infection | 1 (2%), 1 | 0 | 0.33 |
| Hand-foot-and-mouth disease | 6 (10%); 6 | 4 (7%); 4 | 0.53 |
| Herpangina | 2 (3%); 2 | 1 (2%), 1 | 0.58 |
| Acute bronchitis | 1 (2%); 1 | 1 (2%); 1 | 0.99 |
| Exanthema subitum | 4 (7%); 4 | 1 (2%); 1 | 0.32 |
| Acute otitis media | 0 | 3 (5%); 5 | 0.08 |

TABLE 2-continued

| Adverse events" | Placebo (n = 61) | Egg (n = 60) | p value |
|---|---|---|---|
| Otitis media with effusion | 1 (2%); 1 | 0 | 0.33 |
| Impetigo | 2 (3%); 2 | 1 (2%), 1 | 0.58 |
| Suppurative lymphadenitis | 0 | 1 (2%), 1 | 0.31 |

Data are number of patients (%); number of events.
We compared groups with Fisher's exact tests and Wilcoxon rank-sum tests.
RS = respiratory syncytial.
*Defined as more than three events of clinical wheezing.
†Defined as a clear clinical history of immediate allergic reaction.

The present invention is not limited to the description of the embodiments and examples above, but may be altered by a skilled person within the scope of the claims. An embodiment based on a proper combination of technical means disclosed in different embodiments is encompassed in the technical scope of the present invention.

INDUSTRIAL APPLICABILITY

The present invention provides: a method for preventing egg allergy, and a composition for preventing egg allergy.

The invention claimed is:

1. An egg allergy prevention method for preventing a human infant who has not developed an egg allergy from developing an egg allergy, comprising:
a first administration period in which to administer, to the infant, heated egg white protein in an amount of 10 mg to 20 mg per day, wherein the first administration period is not less than 2 and not more than 4 consecutive months, and the infant is from 4 months to less than 10 months of age; and
a second administration period which is a period after the first administration period, wherein the second administration period is not less than 2 and not more than 4 consecutive months, and the infant is from 8 months to not more than 12 months of age, and in which to administer, to the infant, the heated egg white protein in an amount of 65 mg to 90 mg per day,
wherein said infant is an infant who has not developed an egg allergy and who has eczema or has a history of developing eczema.

2. An egg allergy prevention method for preventing a human infant who has not developed an egg allergy from developing an egg allergy, comprising:
a first administration period in which to administer, to the infant, heated whole egg protein in an amount of 20 mg to 30 mg per day, wherein the first administration period is not less than 2 and not more than 4 consecutive months, and the infant is from 4 months to less than 10 months of age; and
a second administration period which is a period after the first administration period, wherein the second administration period is not less than 2 and not more than 4 consecutive months, and the infant is from 8 months to not more than 12 months of age, and in which to administer, to the infant, the heated whole egg protein in an amount of 110 mg to 140 mg per day,
wherein said infant is an infant who has not developed an egg allergy and who has eczema or has a history of developing eczema.

3. An egg allergy prevention method for preventing a human infant who has not developed an egg allergy from developing an egg allergy, comprising:
a first administration period in which to administer, to the infant, dry powder of heated whole egg or a composition containing the dry powder in an amount of 40 mg to 60 mg of the dry powder per day, wherein the first administration period is not less than 2 and not more than 4 consecutive months, and the infant is from 4 months to less than 10 months of age; and
a second administration period which is a period after the first administration period, wherein the second administration period is not less than 2 and not more than 4 consecutive months, and the infant is from 8 months to not more than 12 months of age, and in which to administer, to the infant, the dry powder of the heated whole egg or the composition containing the dry powder in an amount of 220 mg to 280 mg of the dry powder per day,
wherein said infant is an infant who has not developed an egg allergy and who has eczema or has a history of developing eczema.

4. An egg allergy prevention method for preventing a human infant who has not developed an egg allergy from developing an egg allergy, comprising:
a first administration period in which to administer, to the infant, heated whole egg or a composition containing the whole egg in an amount of 0.15 g to 0.25 g of the heated whole egg per day, wherein the first administration period is not less than 2 and not more than 4 consecutive months, and the infant is from 4 months to less than 10 months of age; and
a second administration period which is a period after the first administration period, wherein the second administration period is not less than 2 and not more than 4 consecutive months, and the infant is from 8 months to not more than 12 months of age, and in which to administer, to the infant, the heated whole egg or the composition containing the whole egg in an amount of 0.88 g to 1.25 g of the heated whole egg per day,
wherein said infant is an infant who has not developed an egg allergy and who has eczema or has a history of developing eczema.

5. An egg allergy prevention method for preventing a human infant who has not developed an egg allergy from developing an egg allergy, comprising:
a first administration period in which to administer, to the infant, dry powder of heated egg white or a composition containing the dry powder in an amount of 11 mg to 23 mg of the dry powder per day, wherein the first administration period is not less than 2 and not more than 4 consecutive months, and the infant is from 4 months to less than 10 months of age; and
a second administration period which is a period after the first administration period, wherein the second administration period is not less than 2 and not more than 4 consecutive months, and the infant is from 8 months to not more than 12 months of age, and in which to administer, to the infant, the dry powder of the heated egg white or the composition containing the dry powder in an amount of 75 mg to 104 mg of the dry powder per day, wherein said infant is an infant who has not developed an egg allergy and who has eczema or has a history of developing eczema.

6. The method of preventing egg allergy as set forth in claim 1, wherein the heated egg white protein is orally administered to the infant.

7. The method of preventing egg allergy as set forth in claim 1, further comprising:

a further administration period which is different from each of the first administration period and the second administration period and which is between the first administration period and the second administration period, in the further administration period, the egg white protein being administered to the infant in a greater amount per day than in an administration period followed by the further administration period, and in a smaller amount per day than in an administration period following the further administration period.

8. The method of preventing egg allergy as set forth in claim 1, wherein the heated egg has been heated at a temperature of less than 110° C.

* * * * *